(12) United States Patent
Blum et al.

(10) Patent No.: US 11,602,542 B2
(45) Date of Patent: Mar. 14, 2023

(54) NON-AQUEOUS LIQUID AND SEMI-SOLID FORMULATIONS OF AMORPHOUS CALCIUM CARBONATE

(71) Applicant: AMORPHICAL LTD., Ness Ziona (IL)

(72) Inventors: Yigal Blum, San Jose, CA (US); Yosef Ben, Meshek Ben Arava (IL); Sharon Hershkovitz, Lapid (IL)

(73) Assignee: AMORPHICAL LTD., Ness Ziona (IL)

( * ) Notice: Subject to any disclaimer, the term of this patent is extended or adjusted under 35 U.S.C. 154(b) by 0 days.

(21) Appl. No.: 15/329,677

(22) PCT Filed: Jul. 30, 2015

(86) PCT No.: PCT/IL2015/050788
§ 371 (c)(1),
(2) Date: Jan. 27, 2017

(87) PCT Pub. No.: WO2016/016895
PCT Pub. Date: Feb. 4, 2016

(65) Prior Publication Data
US 2017/0216349 A1    Aug. 3, 2017

Related U.S. Application Data

(60) Provisional application No. 62/031,170, filed on Jul. 31, 2014.

(51) Int. Cl.
| | | |
|---|---|---|
| A61K 33/10 | (2006.01) | |
| C01F 11/18 | (2006.01) | |
| A23L 33/16 | (2016.01) | |
| A23C 9/152 | (2006.01) | |
| A23C 9/13 | (2006.01) | |
| A61K 9/00 | (2006.01) | |
| A61K 9/10 | (2006.01) | |
| A61K 47/14 | (2017.01) | |
| A23C 19/09 | (2006.01) | |
| A61K 47/10 | (2017.01) | |
| A61K 47/26 | (2006.01) | |
| A61K 47/34 | (2017.01) | |
| A61K 47/40 | (2006.01) | |
| A23C 13/12 | (2006.01) | |
| A23C 11/00 | (2006.01) | |
| A23C 19/068 | (2006.01) | |
| A23C 19/076 | (2006.01) | |

(52) U.S. Cl.
CPC ............ *A61K 33/10* (2013.01); *A23C 9/1322* (2013.01); *A23C 9/1522* (2013.01); *A23C 19/0921* (2013.01); *A23L 33/16* (2016.08); *A61K 9/0014* (2013.01); *A61K 9/10* (2013.01); *A61K 47/10* (2013.01); *A61K 47/14* (2013.01); *A61K 47/26* (2013.01); *A61K 47/34* (2013.01); *A61K 47/40* (2013.01); *C01F 11/18* (2013.01); *C01F 11/185* (2013.01); *A23C 11/00* (2013.01); *A23C 13/12* (2013.01); *A23C 19/0684* (2013.01); *A23C 19/0765* (2013.01); *A23V 2002/00* (2013.01); *A23V 2250/032* (2013.01); *A23V 2250/1578* (2013.01); *A23V 2250/1886* (2013.01); *A23V 2250/192* (2013.01); *A23V 2250/5482* (2013.01); *C01P 2002/02* (2013.01); *C01P 2002/72* (2013.01)

(58) Field of Classification Search
None
See application file for complete search history.

(56) References Cited

U.S. PATENT DOCUMENTS

| | | | |
|---|---|---|---|
| 4,005,191 A | 1/1977 | Clark | |
| 4,237,147 A | 12/1980 | Merten | |
| 6,368,638 B1 | 4/2002 | Tiongson | |
| 7,098,178 B2 * | 8/2006 | Gerke | A61K 8/585 510/466 |
| 8,574,564 B2 * | 11/2013 | Renner | A61K 39/39 424/93.2 |
| 2006/0257333 A1 * | 11/2006 | Kauranen | A61K 8/361 424/59 |
| 2008/0199540 A1 * | 8/2008 | Sagi | A61K 33/10 424/687 |
| 2008/0299228 A1 * | 12/2008 | Harris | A61K 9/0014 424/709 |
| 2010/0221262 A1 * | 9/2010 | Koch | C07K 16/2803 424/172.1 |
| 2010/0221362 A1 | 9/2010 | Bentov | |
| 2010/0310677 A1 | 12/2010 | Bentov | |

(Continued)

FOREIGN PATENT DOCUMENTS

| | | |
|---|---|---|
| CA | 2806131 | 2/2012 |
| CN | 101580260 | 11/2009 |

(Continued)

OTHER PUBLICATIONS

Lipke. Clinical Medicine and Research. vol. 4, No. 4, pp. 273-293. Publication year: 2006.*
Taieb et al. British Journal of Dermatology. vol. 168, pp. 5-19. Publication year: 2013.*
Kwon et al. Am J Clin Dermatol. vol. 14, pp. 111-123. Publication year: 2013.*
Hughes et al. British Journal of Pharmacology. vol. 162, pp. 1239-1249. Publication year: 2011.*

(Continued)

*Primary Examiner* — Katherine Peebles
(74) *Attorney, Agent, or Firm* — Dorsey & Whitney LLP

(57) ABSTRACT

The present invention provides stabilized amorphous calcium carbonate (ACC) formulations, comprising ACC and a non-aqueous liquid carrier in which the ACC is dispersed. The present invention further provides cosmetic and pharmaceutical compositions comprising ACC.

5 Claims, 2 Drawing Sheets

(56) References Cited

U.S. PATENT DOCUMENTS

| | | | |
|---|---|---|---|
| 2011/0217358 A1* | 9/2011 | Feleki | A61K 33/06 424/445 |
| 2014/0105937 A1 | 4/2014 | McHale | |
| 2014/0336159 A1* | 11/2014 | Clarke | A61K 9/0075 514/171 |

FOREIGN PATENT DOCUMENTS

| | | | |
|---|---|---|---|
| CN | 101969962 | | 2/2011 |
| DE | 202009013734 | * | 7/2010 |
| JP | H07-196434 A | | 8/1995 |
| JP | 2002-138042 A | | 5/2002 |
| JP | 2008-521754 A | | 6/2008 |
| JP | 2011-529098 A | | 12/2011 |
| KR | 10-2005-0110119 | | 11/2005 |
| WO | 9619228 | | 6/1996 |
| WO | 2004078694 | | 9/2004 |
| WO | 2005097084 | | 10/2005 |
| WO | 2005115414 | | 12/2005 |
| WO | 2007048811 | | 5/2007 |
| WO | 2008041236 | | 4/2008 |
| WO | 2009053967 | | 4/2009 |
| WO | 2012149173 | | 11/2012 |
| WO | 2013088440 | | 6/2013 |
| WO | 2014024191 | | 2/2014 |
| WO | 2014122658 | | 8/2014 |

OTHER PUBLICATIONS

Mayo Clinic Cellulitis Treatment [online]. Mayo Clinic, availiable online from Jan. 7, 2014 [retrieved on Oct. 23, 2017]. Retrieved from the internet: <https://www.mayoclinic.org/diseases-conditions/cellulitis/basics/treatment/con-20023471>.*

Drugs.com Website Boils and Carbuncle [online]. Drugs.com, available online from Aug. 29, 2012 [retrieved on: Oct. 20, 2017]. Retrieved from the internet: <https://www.drugs.com/health-guide/boils-and-carbuncles.html>.*

Machine Translation of Kummer DE 202009013734 [online], Espacenet [retrieved on Mar. 9, 2018] Retrieved from the internet: <www.espacenet.com>. (Year: 2018).*

Goss et al. Journal of Pharmacy and Pharmacology; publication year: 2007. (Year: 2007).*

Truth in Aging website (Calcium as anti-ager) [online]. Truth in Aging, Jan. 13, 2011 [retrieved on Mar. 9, 2018], Retrieved from the internet: <https://www.truthinaging.com/review/calcium-as-an-anti-ager>. (Year: 2011).*

Machine Translation of Tazuko H07-196434 [online], Tazuko [retrieved on Sep. 6, 2019], Retrieved from the internet: <www.epo.org> (Year: 1995).*

Human translation of Tazuko JP 07196434, pp. 1-13. Provided to the USPTO by Schreiber Translations, Inc. Nov. 2019 (Year: 2019).*

Bentov et al., (2010) Stabilization of amorphous calcium carbonate by phosphate rich organic matrix proteins and by single phosphoamino acids. J Struct Biol 171(2): 207-15.

Clarkson et al., (1992) Role of metastable phases in the spontaneous precipitation of calcium carbonate. J Chem Soc, Faraday Trans 88(2): 243-249.

Hecker et al., (2003) Phosphorylation of serine residues is fundamental for the calcium-binding ability of Orchestin, a soluble matrix protein from crustacean calcium storage structures. FEBS Lett 535(1-3): 49-54.

Hu et al., (2010) Strongly bound citrate stabilizes the apatite nanocrystals in bone. Proc Natl Acad Sci USA 107(52): 22425-22429.

Huang et al., (2007) A carbonate conliolled-addition method for amorphous calcium carbonate spheres stabilized by poly(acrylic acid)s. Langmuir 23: 12086-12095.

Johnsson et al., (1991) Adsorption and mineralization effects of citrate and phosphocitrate on hydroxyapatite. Calcif Tissue Int 49(2): 134-137.

Koga et al., (1998) Crystallization of amorphous calcium carbonate. Thermochimica Acta 318(1-2): 239-244.

Lee et al., (2005) Fabrication of unusually stable amorphous calcium carbonate in an ethanol medium. Materials Chemistry and Physics 93(2-3): 376-382.

Loste et al., (2003) The role of magnesium in stabilising amorphous calcium carbonate and controlling calcite morphologies. Journal of Crystal Growth 254(1-2): 206-218.

Malkaj and Dalas (2007) The effect of acetaminophen on the crystal growth of calcium carbonate. J Mater Sci Mater Med 18(5): 871-875.

Manoli and Dalas (2002) The effect of sodium alginate on the crystal growth of calcium carbonate. J Mater Sci Mater Med 13(2): 155-158.

Martins et al., (2008) Hydroxyapatite micro-and nanoparticles: nucleation and growth mechanisms in the presence of citrate species. J Colloid Interface Sci 318(2): 210-216.

Maruyama et al., (2011) Synthesizing a composite material of amorphous calcium carbonate and aspartic acid. Materials Letters 65(2): 179-181.

Meiron et al., (2011) Solubility and bioavailability of stabilized amorphous calcium carbonate. Journal of Bone and Mineral Research, 26(2), 364-372.

Multigner et al., (1983) Pancreatic stone protein, a phosphoprotein which inhibits calcium carbonate precipitation from human pancreatic juice. Biochemical And Biophysical Research Communications 110(1): 69-74.

Reddi et al., (1980) Influence of phosphocitrate, a potent inhibitor of hydroxyapatite crystal growth, on mineralization of cartilage and bone. Biochem Biophys Res Commun 97(1): 154-159.

Rodriguez-Blanco et al., (2008) How to make 'stable' ACC: protocol and preliminary structural characterization. Mineralogical Magazine 72(1): 283-286.

Rodriguez-Blanco et al., (2012) The role of pH and Mg on the stability and crystallization of amorphous calcium carbonate. Journal of Alloys and Compounds 536(Supp 1): S477-S479 International Symposium on Metastable, Amorphous and Nanostructured Materials, ISMANAM-2011 (Jun. 26 to Jul. 1, 2011).

Saitoh et al., (1985) Inhibition of calcium-carbonate precipitation by human salivary proline-rich phosphoproteins. Arch Oral Biol 30(8): 641-643.

Sawada (1997) The mechanisms of crystallization and transformation of calcium carbonates. Pure & Appl Chem 69(5): 921-928.

Schneiders et al., (2007) Effect of modification of hydroxyapatite/collagen composites with sodium citrate, phosphoserine, phosphoserine/RGD-peptide and calcium carbonate on bone remodelling. Bone 40(4): 1048-1059.

Shechter et al., (2008) A gastrolith protein serving a dual role in the formation of an amorphous mineral containing extracellular matrix. Proc Natl Acad Sci U S A 105(20): 7129-7134.

Thomas and Biichall (1983) The retarding action of sugars on cement hydration. Cement and Concrete Research 13(6): 830-842.

Vaisanen H "CaCO3 scale inhibition in paper making processes—evaluation of testing methods and inhibitor performance". Master's thesis; Tampere University of Technology, Dec. 2011. 103 pages.

Xie et al., (2010) Influence of viscosity on the phase transformation of amorphous calcium carbonate in fluids: An understanding of the medium effect in biomimetic mineralization. Science China Chemistry, 53(10), 2208-2214.

Xurong et al., (2008) Amorphous Calcium Carbonate in Biomineralization. Progress in Chemistry 20(1): 54-59.

Segur & Oberstar, (1951) Viscosity of glycerol and its aqueous solutions. Industrial & Engineering Chemistry, 43(9), 2117-2120.

Chick and Borah (1990) Calcium carbonate gel therapy for hydrofluoric acid burns of the hand. Plast Reconstr Surg 86(5): 935-940.

Muller et al., (2017) A Novel Biomimetic Approach to Repair Enamel Cracks/Carious Damages and to Reseal Dentinal Tubules by Amorphous Polyphosphate. Polymers (Basel) 9(4): 120; 21 pages.

(56) References Cited

OTHER PUBLICATIONS

Yasue et al., (1985) Synthesis and Characteristics of Amorphous Calcium Carbonate in Ethanol. Gypsum & Lime 1985(198): 245-252. Abstract.
"Clinical Dermatovenereal Disease", the 1st edition, Wang Aiqin, et al., Scientific and Technical Documents Publishing House, paragraph 1 in the right column on p. 35, May 31, 2014. English translation of relevant parts.
Handbook of Dermatological External Preparations, the 1st edition, Peng Guomin, People's Medical Publishing House, Unguentum Picis Pini Compositum on pp. 102-103, Aug. 31, 1984. English translation of relevant parts.
"Pharmaceutics", the 1st edition, Guo Hulling, Sun Yat-Sen University Press, paragraph 1 on p. 248-paragarph 2 on p. 250, Feb. 28, 2014. English translation of relevant parts.

\* cited by examiner

NON-AQUEOUS LIQUID AND SEMI-SOLID FORMULATIONS OF AMORPHOUS CALCIUM CARBONATE

FIELD OF THE INVENTION

The present invention relates to non-aqueous, liquid or semi-solid compositions comprising amorphous calcium carbonate (ACC), and methods for their use in therapy.

BACKGROUND OF THE INVENTION

Calcium is considered to be one of the most important minerals in the human body. It is required for maintaining bone mineral density, essential for exocytosis of neurotransmitters, takes part in the contraction of muscle cells, replaces sodium as the depolarizing mineral in the heart, and participates in many other physiological functions. Calcium carbonate—an inorganic phase of calcium—is an authorized food additive and the main compound form commercially used in the nutrient supplement market. Calcium carbonate has six known polymorphs, three of which are anhydrous crystalline (i.e., calcite, aragonite, and vaterite), two of which are hydrated (i.e., crystalline monohydrocalcite and ikaite), and one of which is hydrated amorphous, namely, amorphous calcium carbonate (ACC). The most thermodynamically stable of these phases is calcite, whereas the least stable is ACC. ACC is a transient polymorph that precipitates out of a supersaturated solution following Ostwald's step rule. If not stabilized by any element or compound, ACC will crystallize rapidly and completely into one of the five more stable polymorphs within seconds. Solubility studies suggest dramatic differences between the calcium carbonate polymorphs: while crystalline phases are considered poorly soluble, the amorphous polymorph is approximately 120 times more soluble than calcite.

Several techniques have been reported for the synthesis and stabilization of ACC, including using phosphoaminoacids, which allowed stabilizing ACC for more than 4 months under ambient conditions (Meiron et al., J. Bone Min. Res., 2011, Vol. 26(2), pages 364-372). In nature, ACC is utilized by a small number of organisms, mainly crustaceans and other invertebrates that developed capabilities for stabilizing ACC in transient mineral deposition sites. These organisms require an exceptional efficient mineral source for the periodical mobilization, absorption and precipitation of calcium. In some crustaceans, such as the freshwater crayfish, ACC is stored in large quantities in specialized transient storage organs, named the gastrolith.

Various uses of stabilized ACC (sACC) are known, including oral formulations for administration as a food supplement and/or as a medicament. Additionally, formulations of stable ACC are generally provided as dry material. WO 2005/115414 discloses for example gastrolith organs, ground to a fine powder, which are useful as pharmaceutical and nutraceutical calcium compositions. WO 2009/053967 is directed, inter alia, to pharmaceutical and nutraceutical compositions comprising synthetic ACC stabilized by phosphorylated peptides or amino acids. WO 2014/024191 encompasses among other things a method for preparing a stable amorphous calcium carbonate, which can be obtained either in suspension or as a powder. The method comprises stepwise combination of a soluble calcium salt, a soluble carbonate, a first and second stabilizer, and a water miscible organic solvent.

There is an unmet need for non-aqueous, liquid or semi-solid formulations of ACC, in which ACC remains stable for extensive periods of time, which can be used, for example, as topical remedies.

SUMMARY OF THE INVENTION

The present invention relates to liquid and semi-solid formulations comprising ACC, which are substantially devoid of water. The present invention demonstrates that ACC may be provided as a stable dispersion in a biocompatible non-aqueous medium, and effectively prevent, treat or ameliorate a variety of human adversities. It has been surprisingly found that the dispersed ACC particles remain stable in amorphous form in the formulation for prolonged periods of time even without being encapsulated in a protective solid matrix. The dispersing vehicles according to the principles of the present invention may therefore be used instead of, or in addition to, the known stabilizing agents of amorphous calcium carbonate. In addition, the liquid and semi-solid formulations of the present invention are homogenous, i.e. the ACC particles are homogeneously dispersed throughout the dispersion medium.

The formulations provided by the present invention may advantageously be administered by a topical route (for example as an ointment, lotion, cream, gel, paste, suppository), or in the form of drops (such as nasal drops, eye drops or oral drops). According to the principles of the present invention, the ACC formulations may also be administered by an oral route, for example, be packed in capsules for oral administration. The inventors demonstrate that both liquid and semi-solid formulations according to the principles of the present invention may be safely administered to mammalian subjects, including topical administration on the skin and/or mucous membranes. The inventors have further shown that these non-aqueous, topical formulations were effective in the treatment of inflammation driven by cell-mediated immunity.

The present invention provides, in one aspect, a liquid or semi-solid non-aqueous composition in the form of a dispersion or suspension of amorphous calcium carbonate (ACC) particles, comprising: a plurality of ACC particles comprising ACC and at least one agent stabilizing the ACC in amorphous form, and a non-aqueous liquid carrier in which the ACC particles are insoluble and are substantially uniformly dispersed or suspended.

The present invention further provides a liquid or semi-solid non-aqueous composition in the form of a dispersion or suspension of amorphous calcium carbonate (ACC) particles, comprising: a plurality of ACC particles comprising ACC and at least one agent stabilizing the ACC in amorphous form, and a non-aqueous liquid carrier in which the ACC particles are insoluble and are substantially uniformly dispersed or suspended; the composition having a viscosity of above 40 centipoise (cP) at 25° C.

The present invention further provides a liquid or semi-solid non-aqueous composition in the form of a dispersion or suspension of amorphous calcium carbonate (ACC) particles, comprising: a plurality of ACC particles comprising ACC and at least one agent stabilizing the ACC in amorphous form, the particles having an average particle size in the longest dimension of about 0.1 μm to about 100 μm; and a non-aqueous liquid carrier in which the ACC particles are insoluble and are substantially uniformly dispersed or suspended; the composition having a viscosity of above 40 cP at 25° C. and comprising less than about 10% by weight water of the total composition.

The present invention further provides a liquid or semi-solid non-aqueous composition in the form of a dispersion or suspension of amorphous calcium carbonate (ACC) particles, comprising: a plurality of ACC particles comprising ACC and at least one agent stabilizing the ACC in amorphous form, the particles having an average particle size in the longest dimension of about 0.1 µm to about 100 µm; and above 30% by weight of the total composition comprises a non-aqueous liquid carrier in which the ACC particles are insoluble and are substantially uniformly dispersed or suspended; the composition having a viscosity of above 40 cP at 25° C. and comprising less than about 10% by weight water of the total composition.

The present invention further provides a liquid or semi-solid non-aqueous composition in the form of a dispersion or suspension of amorphous calcium carbonate (ACC) particles, comprising: a plurality of ACC particles comprising ACC and at least one agent stabilizing the ACC in amorphous form, the particles having an average particle size in the longest dimension of about 0.1 µm to about 100 µm; and above 50% by weight of the total composition comprises a non-aqueous liquid carrier in which the ACC particles are insoluble and are substantially uniformly dispersed or suspended; the composition having a viscosity of above 40 cP at 25° C. and comprising less than about 10% by weight water of the total composition.

In certain embodiments, the viscosity of the composition at 25° C. is above 100 cP, above 1,000 cP, above 10,000 cP, or above 100,000 cP. In certain embodiments, the viscosity of the composition at 25° C. is about 100 cP to about 50,000 cP, about 1,000 cP to about 30,000 cP, or about 2,000 cP to about 20,000 cP. In certain embodiments, the viscosity of the composition at 25° C. is about 1,000 cP to about 300,000 cP, about 10,000 cP to about 200,000 cP, or about 30,000 cP to about 100,000 cP. Each possibility represents a separate embodiment of the invention.

In certain embodiments, the ACC particles have an average particle size of their longest dimension of about 0.1 µm to about 100 µm, or about 0.1 µm to about 10 µm. In certain embodiments, the ACC particles have an average particle size of their longest dimension of below 100 µm, or below 10 µm. Each possibility represents a separate embodiment of the invention.

In certain embodiments, the compositions of the present invention comprise less than about 10% by weight water of the total composition. In certain embodiments, the compositions of the present invention comprise less than about 5% by weight water of the total composition. In certain embodiments, the compositions of the present invention comprise less than about 3% by weight water of the total composition.

In certain embodiments, the compositions of the present invention comprise at least about 0.01%, at least about 0.1%, at least about 1% or at least about 10% by weight ACC of the total composition. In certain embodiments, the compositions of the present invention comprise about 0.01 to about 40%, about 0.01 to about 10%, about 0.1 to about 10%, or about 1 to about 10% by weight ACC of the total composition. Each possibility represents a separate embodiment of the invention.

In certain embodiments, the non-aqueous liquid carrier is selected from the group consisting of organic polyols, water-immiscible lipids, synthetic oils, and mixtures thereof. In certain embodiments, the non-aqueous liquid carrier comprises an organic polyol, a water-immiscible lipid, a synthetic oil, or any combination thereof. Each possibility represents a separate embodiment of the invention.

In certain embodiments, the organic polyol is selected from the group consisting of propylene glycol (PG), a polyethylene glycol (PEG), a PEG derivative, glycerol, and any combination thereof. In certain embodiments, the organic polyol is selected from the group consisting of propylene glycol (PG), a polyethylene glycol (PEG), a PEG derivative, and any combination thereof. In certain embodiments, the PEG is selected from the group consisting of PEG 100, PEG 200, PEG 300, PEG 400, PEG 500, PEG 600, PEG 700, PEG 800, PEG 900, and any combination thereof. In certain embodiments, the PEG is selected from the group consisting of a "branched" PEG having 3-10 PEG chains emanating from a central core group, a "star" PEG having 10-100 PEG chains emanating from a central core group, and a "comb" PEG having multiple PEG chains linked to a polymer backbone. Each possibility represents a separate embodiment of the invention.

In certain embodiments, the water-immiscible lipid is selected from the group consisting of a natural oil, a medium-chain triglyceride, and any combination thereof. In certain embodiments, the natural oil is selected from the group consisting of castor oil, corn oil, cottonseed oil, olive oil, peanut oil, peppermint oil, sunflower oil, sesame oil, soybean oil, hydrogenated vegetable oils, hydrogenated soybean oil, and combinations thereof. In certain embodiments, the medium-chain triglyceride comprises medium-chain triglycerides of coconut oil or palm seed oil. In certain embodiments, the natural oil is a glyceride. In certain embodiments, the glyceride is hydrogenated. In certain embodiments, the glyceride is selected from a mono-, di- or tri-glyceride. In certain embodiments, the glyceride is a long chain glyceride.

According to some embodiments, the medium-chain glycerides include medium-chain glycerides of coconut oil or palm seed oil. The composition may comprise about 5-50% w/w medium chain triglycerides. In some embodiments, the composition comprises about 10-40% w/w medium chain triglycerides, such as about 15-35% w/w medium chain triglycerides or about 15, 18 or 33% medium chain triglycerides. Each possibility represents a separate embodiment of the invention.

In certain embodiments, the synthetic oil is selected from the group consisting of a polydimethylsiloxane, a functionally modified dimethylsiloxane, a polydimethylsiloxane-copolyol, a polydimethylsiloxane-crosspolymer, and combinations thereof. In certain embodiments, the polydimethylsiloxane is linear. In certain embodiments, the polydimethylsiloxane is cyclic. In certain embodiments, the polydimethylsiloxane is selected from the group consisting of a cyclopentasiloxane, a cyclotetrasiloxane, and combinations thereof. In certain embodiments, the functionally modified dimethylsiloxane is a siloxane monomer modified by independently replacing one or two methyl groups with an H, OH, phenyl, propyl, octyl, amino-propyl, or vinyl. In certain embodiments, the polydimethylsiloxane-copolyol is cyclopentasiloxane and a mixture of PEG/PPG-18/18 dimethicone. In certain embodiments, the polydimethylsiloxane-crosspolymer is a cyclopentasiloxane and a mixture of dimethicone crosspolymer. Each possibility represents a separate embodiment of the invention.

In certain embodiments, the compositions described above further comprise at least one excipient selected from the group consisting of a surfactant, an emollient, a thickening agent and a dispersing agent.

In certain embodiments, the surfactant is a non-ionic organic surfactant or an anionic organic surfactant. In certain embodiments, the non-ionic organic surfactant is selected from the group consisting of polysorbates, sorbitan esters, fatty acid esters, wax esters, poloxamers, and phospholipids. In certain embodiments, the polysorbates are selected from the group consisting of Tween 80, Tween 60, Tween 40, Tween 20, and combinations thereof. In certain embodiments, the fatty acid esters are selected from the group consisting of polyoxyethylene fatty acid esters, sucrose esters of fatty acids, glycerol monostearate, and combinations thereof. In certain embodiments, the fatty acid esters are selected from the group consisting of Span 80, Span 60, Span 40, Span 20, Sisterna, Cutina, MYRJ 52, solutol HS15, and combinations thereof. In certain embodiments, the wax ester is isostearyl isostearate. In certain embodiments, the anionic organic surfactant is sodium lauryl sulfate. Each possibility represents a separate embodiment of the invention.

In certain embodiments, the emollient is selected from the group consisting of a wax, a solid fat, a glyceride, an ethoxylated fatty alcohol, and combinations thereof. In certain embodiments, the thickening agent is selected from the group consisting of a cellulose polymer, silsesquioxane, silica, and combinations thereof. In certain embodiments, the cellulose polymer is selected from the group consisting of hydroxypropylethylcellulose, sodium carboxymethyl cellulose, and combinations thereof. In certain embodiments, the dispersing agent is a cyclodextrin. In certain embodiments, the cyclodextrin is selected from the group consisting of α-cyclodextrin, β-cyclodextrin, γ-cyclodextrin, and combinations thereof. Each possibility represents a separate embodiment of the invention.

In certain embodiments, the at least one ACC stabilizing agent is selected from the group consisting of an organic acid, a sulfuric ester of a hydroxyl carboxylic acid, a sulfuric ester of a hydroxyl carboxylic acid, an organoamine compound, an organic compound comprising a hydroxyl, an organophosphorous compound or a salt thereof, a bisphosphonate compound, an organophosphate compound, an organophosphonate compound, an inorganic phosphorous acid, a polyphosphate compound, an organic surfactant, a bio-essential inorganic ion, and any combination thereof. Each possibility represents a separate embodiment of the invention.

The present invention further provides, in another aspect, a cosmeceutical composition comprising any one of the compositions described above.

The present invention further provides, in another aspect, a pharmaceutical composition comprising any one of the compositions described above.

In certain embodiments, the pharmaceutical composition described above is for use in treating or ameliorating a topical inflammation or for use in treating or ameliorating a skin affliction.

The present invention further provides, in another aspect, a topical pharmaceutical composition comprising stabilized ACC, formulated for topical administration, for use in treating or ameliorating a topical inflammation or for treating or ameliorating a skin affliction.

In certain embodiments, the inflammation is associated with an auto-immune reaction. In certain embodiments, the skin affliction is psoriasis. In certain embodiments, the skin affliction is psoriasis, and at least one clinical parameter selected from the group consisting of erythema (redness), induration (thickness) and desquamation (scaling) is prevented or ameliorated.

The present invention further provides, in another aspect, a method of treating or ameliorating a topical inflammation or a skin affliction in a patient in need, comprising the step of topically administering to the patient a therapeutically effective amount of stabilized ACC.

In certain embodiments, the methods described above comprise the step of topically administering to the patient a therapeutically effective amount of a non-aqueous ACC composition as disclosed herein.

All the above and other characteristics of the invention and of embodiments thereof will be further understood through the following illustrative and non-limitative description of embodiments thereof, with reference to the appended drawings.

DETAILED DESCRIPTION OF THE INVENTION

Figure 1A:
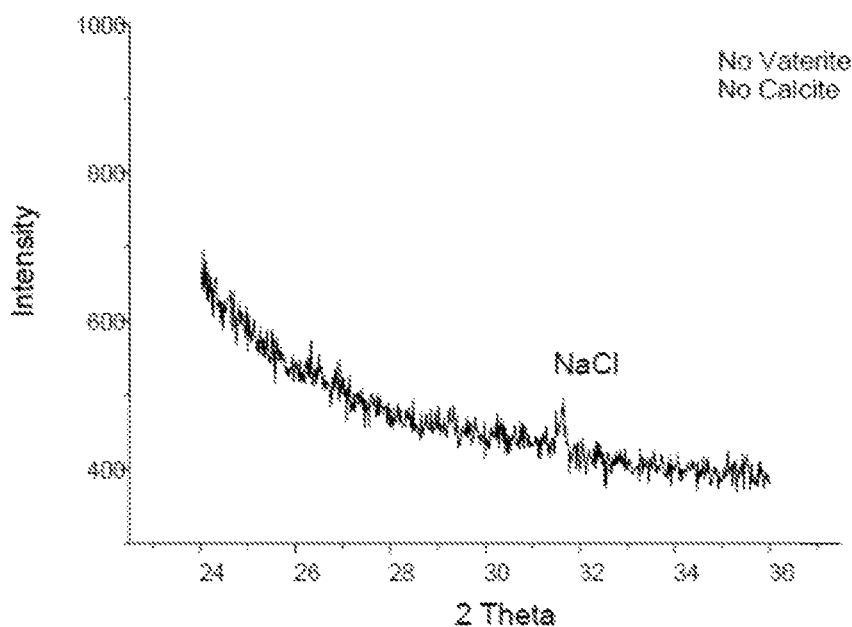
FIG. 1A. XRD pattern of ACC Formulation #5.

The present invention provides non-aqueous liquid and semi-solid formulations comprising amorphous calcium carbonate (ACC). The liquid formulations of the present invention comprise a dispersing vehicle (phase), in which ACC, while being insoluble, is stable and homogeneously dispersed. The formulations may be administered to a human subject parenterally, topically or enterally and can be formulated in various dosage forms. Thus, the ACC formulations provide the benefits of an amorphous form of calcium carbonate, such as an enhanced bioavailability of calcium, when administered to a human subject. To the inventors' best knowledge, stable topical or parenteral formulations including amorphous calcium carbonate have not been previously contemplated or demonstrated.

The ACC formulations provided by the present invention encompass several advantages over other ACC compositions and formulations previously disclosed. For example, since ACC is notoriously known to be highly unstable in aqueous environments, the present formulations provide non-aqueous, stabilizing environments to the ACC. Further, biological agents do not thrive in non-aqueous environments and therefore non-aqueous formulations may be prepared and stored with substantially no preservatives. More, typically, non-aqueous formulations do not evaporate and/or drip as easily as aqueous ones, which would extend the contact time between the formulations and the tissue(s) to which they are applied. Silicone-based formulation, for example, may be easily spread and stay adhered to the skin even after extended exposure to water e.g. when bathing or swimming in a pool or at sea. In addition, using silicones provide a silky feel to the formulation, which appeal to users and be easier to spread than stickier suspensions.

In obtaining the formulations provided by the present invention, the inventors overcame several technical difficulties which hindered, thus far, the development of non-solid stable ACC formulations. For example, when formulating an aqueous emulsion, one may use the Hydrophilic-lipophilic balance (HLB) values known for many compounds, which are used to guide the selection of surfactant for a particular suspension/emulsion that usually contains oil and water. However, this value does not provide a good guideline for making a non-aqueous emulsion. More, anhydrous formulations are often sticky and greasy. Homogeneity is also important, because aggregates may cause severe side effects.

Methods for overcoming these technical pitfalls, and others, are provided by the present invention.

In the formulations of the present invention, the ACC retains its amorphous form for long periods of time. Without being bound to any theory or mechanism, this enhanced stability may be attributed to the hydrophobic nature of the dispersing vehicle. The choice of the dispersing vehicle is dictated inter alia by its ability to homogeneously disperse ACC, while preserving the ACC's amorphous state and preventing its dissolution in the dispersing vehicle. Preferably, the dispersing vehicle used in the formulations of the present invention is a pharmaceutically acceptable vehicle and as such it allows administration of the formulations to a human subject via a parenteral, topical or enteral route. The dispersing vehicle may further be selected to allow release of the ACC in the desired body organ and/or facilitate calcium absorption therein.

The present invention provides, in one aspect, a liquid or semi-solid non-aqueous composition in the form of a dispersion or suspension of amorphous calcium carbonate (ACC) particles, comprising: a plurality of ACC particles comprising ACC and at least one agent stabilizing the ACC in amorphous form, and a non-aqueous liquid carrier in which the ACC particles are insoluble and are substantially uniformly dispersed or suspended.

The term "dispersion" as used herein is a system in which ACC particles are dispersed in a continuous phase of a non-aqueous liquid carrier. The term "suspension" as used herein is a system in which ACC particles are dispersed throughout a non-aqueous liquid carrier through mechanical agitation, with the use of certain excipients or suspending agents. The suspension can be mechanically agitated by the end-user in order to allow homogeneous dispersion of the ACC particles in the non-aqueous liquid carrier.

According to some embodiments, the composition is in a form of a colloid. As used herein, the term "colloid" relates to a homogeneous dispersion of ACC particles in a continuous non-aqueous liquid carrier. According to some embodiments, the ACC particles cannot be separated from the continuous non-aqueous liquid carrier by ordinary filtering or centrifuging like those in a suspension. According to further embodiments, the ACC particles do not settle or float in the colloid.

As used herein, the term "colloid" further relates to microscopically dispersed sACC particles in a continuous liquid carrier. According to some embodiments, the colloid is a homogeneous colloid. The term "homogeneous colloid", as used herein, refers to a dispersion of the stabilized ACC in the continuous liquid carrier, wherein substantially uniform distribution of the ACC particles is possible throughout the colloid. According to some embodiments, the sACC particles are homogeneously dispersed throughout the colloid for at least about 2 days. According to further embodiments, the ACC particles do not float or settle in the colloid. The dispersing vehicle of the colloid may comprise one or more non-aqueous solvents, wherein said solvents are generally miscible.

According to some embodiments, the colloid further comprises a dispersing agent that maintains the homogeneous dispersion of the ACC particles throughout the colloid. In addition, the dispersing agent, in some embodiments, prevents or reduces sedimentation or floating of the ACC particles in the colloid.

In certain embodiments, the non-aqueous liquid carrier can be in a form of a viscous liquid, paste, an emulsion or a gel. While the terms "suspension" and "colloid" refer to the form of distribution of the ACC particles in the non-aqueous liquid carrier, the terms "emulsion", "paste" and "gel" relate to the appearance of the non-aqueous liquid carrier.

As used herein, the term "emulsion", relates to a non-aqueous liquid carrier containing two or more liquid immiscible phases, one of which is a dispersed phase and another one is a continuous phase, wherein the dispersed phase is dispersed in the continuous phase in the form of droplets. The ACC particles can be dispersed in any one of the immiscible phases. The emulsion can be in a form of a macro-emulsion, a micro-emulsion or a nano-emulsion.

As used herein, the term "emulsion" further relates to a dispersion of ACC particles in a composition containing two or more liquid immiscible phases, one of which is a dispersed phase and another one is a continuous phase, wherein the dispersed phase is dispersed in the continuous phase in the form of droplets. The ACC particles can be dispersed in any one of the immiscible phases. Thus, according to some embodiments, the liquid carrier of the emulsion comprises at least two non-aqueous solvents, wherein said solvents are immiscible.

According to some embodiments, the emulsion is a homogeneous emulsion. The term "homogeneous emulsion", as used herein, refers to a dispersion of the stabilized ACC in the continuous phase of the emulsion or in the dispersed phase of the emulsion, wherein substantially uniform dosing of the ACC particles is possible throughout the emulsion, and therefore the dosing can be predicted and predetermined. According to some embodiments, the ACC particles are homogeneously dispersed throughout the emulsion for at least about 6 months.

According to some embodiments, the emulsion is a stable emulsion. As used herein, the term "stable emulsion" refers to a dispersion of ACC particles in the continuous phase of the emulsion or in the dispersed phase of the emulsion, wherein the ACC particles remain in emulsion, with no visible floating or sedimentation. Alternatively, the term "stable emulsion" refers to the two or more immiscible phases, which remain associated for at least about 6 months.

According to some embodiments, the emulsion comprises a hydrophilic liquid and a lipophilic liquid. In some embodiments, the ACC particles are dispersed in the hydrophilic liquid. In further embodiments, the hydrophilic liquid is dispersed in the lipophilic liquid continuous phase. Alternatively, the lipophilic liquid is dispersed along with the ACC particles in the hydrophilic liquid continuous phase. In some embodiments, the ACC particles are dispersed in the hydrophobic liquid. In further embodiments, the lipophilic liquid is dispersed in the hydrophilic liquid continuous phase. Alternatively, the hydrophilic liquid is dispersed along with the ACC particles in the lipophilic liquid continuous phase.

The emulsion can be in a form of a macro-emulsion, micro-emulsion or nano-emulsion. Each possibility represents a separate embodiment of the invention.

Microemulsions and nanoemulsions, in contrast to macroemulsions, appear translucent, due to their smaller droplet size. As used herein, the term "microemulsion" refers to a translucent, thermodynamically stable mixture of a hydrophobic liquid, a hydrophilic liquid, and an amphiphilic component. Typically, a microemulsion forms spontaneously when the components are combined and mixed with each other, without requiring high energy input as is normally required for the formation of a macro-emulsion. Microemulsions may have a colloidal lipophilic phase dispersed in a hydrophilic phase, or a hydrophilic phase colloidally dispersed in a lipophilic phase. The size of the dispersed phases is usually in the range from about 5 nm to about 400 nm, and most often below about 200 nm. In some embodiments, the particle size is from about 5 nm to about 100 nm. As used herein, the term "nanoemulsion" refers to nanoscale dispersions of droplets of one liquid in another immiscible liquid. In contrast to microemulsions, nanoemulsions require specialized equipment to be produced, but a smaller amount of an amphiphilic component.

According to some embodiments, the emulsion further includes a surfactant or an emulsifier. Addition of the surfactant allows mixing of the two or more liquid immiscible phases, producing an emulsion. Addition of the surfactant further allows the emulsion stabilization. According to some embodiments, the surfactant assists in the homogeneous dispersion of the ACC particles throughout the emulsion.

As used herein, the term "paste", relates to a viscous thick liquid. The paste can be thick due to the nature of the non-aqueous liquid carrier used, such as, for example, glycerin, or to the addition of excipients, such as, for example, thickeners.

As used herein, the term "gel", relates to a non-aqueous liquid carrier containing a dispersion of molecules of a liquid within a solid in which the solid is the continuous phase and the liquid is the discontinuous phase. According to some embodiments, the ACC particles are dispersed in the liquid discontinuous phase.

The term "ACC particle" as used herein refers to a combination of ACC and an ACC stabilizing agent. Unless specifically otherwise indicated, the disclosed ACC content (% by weight) of the compositions provided by the present invention refers to the amount of ACC particles.

As used herein, the terms "stabilized ACC", "sACC" or "stabilized form of ACC" relates to a composition comprising ACC and at least one stabilizing agent, such that the stable form of ACC has an increased stability in dry conditions as compared to pure ACC, without a stabilizer. The term "stable ACC" is used herein to indicate that the calcium carbonate may be maintained in substantially dry conditions in amorphous state thereof for long periods of time, e.g., from several weeks to several years, with no more than about 20% conversion into the crystalline phase over the period of time.

The terms "amorphous phase", "amorphous form" and "amorphous state" can be used interchangeably. The terms "amorphous calcium carbonate", "amorphous phase of calcium carbonate", "amorphous form of calcium carbonate" and "amorphous state of calcium carbonate" can be used interchangeably, and indicate a polymorph which is in a phase, form or state which is not in any of the crystalline forms of calcium carbonate.

The terms "ACC stabilizer" or "ACC stabilizing agent" as used herein are used interchangeably and refer to any substance that contributes to preserving amorphous calcium carbonate in the amorphous state in substantially dry conditions. The terms "stabilizer" or "stabilizing agent" as used herein are used interchangeably and refer to any substance that contributes to preserving non-encapsulated calcium carbonate in the amorphous state in substantially dry conditions. "Substantially dry conditions" or "dry" refers, in some embodiments, to an environment containing less than 20% wt. water relatively to the total weight of the stabilized ACC.

As used herein, the term "non-aqueous" is intended to refer to formulations having a water content of about 20% by weight or less. The term "liquid carrier" as used herein means the combination of all excipients used in the formulation, and specifically excludes ACC. The term "excipient" as used herein denotes a non-therapeutic agent added to ACC, e.g. to provide a desired viscosity, consistency, stability or any other desired effect. In certain embodiments, the term refers to a formulation manufactured without the use of any aqueous solvents.

The term "liquid carrier" further includes all the excipients described by the present invention which are liquid in ambient temperature alone, i.e. when not mixed with the ACC particles or any other excipient. The term "liquid carrier" further includes all the excipient combinations described by the present invention which are liquid in ambient temperature, i.e. when mixed with the ACC particles.

According to some embodiments, the liquid carrier comprises at least two organic liquids. According to some embodiments, the at least two organic solvents are miscible. In certain such embodiments, the composition is in a form of a suspension. According to some embodiments, the at least two organic solvents are immiscible. In certain such embodiments, the at least two organic liquids form an emulsion.

The phrase "dispersed or suspended" is intended to mean that a homogenous composition is formed. The phrase encompasses, but is not limited to, all forms of solutions, dispersions, suspensions or emulsions.

According to some embodiments, the composition is homogeneous. The terms "homogeneous" or "ACC particles, which are homogeneously dispersed or suspended", as used herein, refer to a dispersion or suspension of the stabilized ACC in the non-aqueous liquid carrier, wherein the ACC particles are substantially distributed throughout the non-aqueous liquid carrier. According to some embodiments, the ACC particles are homogeneously dispersed throughout the composition following mechanical agitation, such as, for example, shaking. According to some embodiments, the ACC particles are homogeneously dispersed throughout the composition for at least 2 hours, preferably at least 12 hours, from the composition preparation. According to yet further embodiments, the concentration of agglomerated particles in the homogeneous formulation remains substantially constant.

According to some embodiments, the composition is stable. As used herein, the term "stable composition" refers to a dispersion of the ACC particles in the non-aqueous liquid carrier, wherein the ACC particles remain in the non-aqueous liquid carrier with no visible floating or sedimentation. According to some embodiments, the ACC particles remain in the non-aqueous liquid carrier with no visible floating or sedimentation for at least 2 hours, for example 2 hours from re-suspension.

According to some embodiments, the suspension is a stable suspension. As used herein, the term "stable suspension" refers to a dispersion of the sACC particles in a continuous liquid carrier, wherein the sACC particles remain in suspension, with no visible floating or sedimentation. According to some embodiments, the sACC particles remain in suspension, with no visible floating or sedimentation for at least 12 hours from the suspension preparation.

The present invention further provides a liquid or semi-solid non-aqueous composition in the form of a dispersion or suspension of amorphous calcium carbonate (ACC) particles, comprising: a plurality of ACC particles comprising ACC and at least one agent stabilizing the ACC in amorphous form, and a non-aqueous liquid carrier in which the ACC particles are insoluble and are substantially uniformly dispersed or suspended; the composition having a viscosity of above 40 centipoise (cP) at 25° C.

As used herein, the term "viscosity" generally relates to a measure of a material's resistance to gradual deformation by stress. As used herein, the term "cP" refers to a centipoise. A centipoise is a measure of the viscosity of a material, and is one one-hundredth of a poise, or one millipascal-second (mPa·s). The term "dynamic (shear) viscosity" as used herein refers to a material's to shearing flows, where adjacent layers move parallel to each other with different speeds.

Several techniques may be employed to determine the viscosity of a material, using a variety of apparatuses under different conditions. This variability, in turn, may provide a wide range of viscosity values for substantially the same material. According to the principles of the present invention, the viscosity of the compositions and formulation provided by the present invention is determined at ambient temperature (about 25° C.) by a rotational viscometer. The rotational viscometer measures the torque required to turn an object in a fluid as a function of that fluid's viscosity. This method is frequently used in quality control and production laboratories. A non-limiting example of a method used to determine the viscosity of the compositions and formulation provided by the present invention is provided in the Examples section below. More specifically, in certain embodiments, the viscosity is measured at room temperature (24.8° C.) using Brookfield Digital Viscometer Model DV-II+Pro and Spindle #16 at rotation speeds of 1 rpm, 1.5 rpm and/or 2 rpm.

In certain embodiments, the viscosity of the composition at 25° C. is above 100 cP, above 1,000 cP, above 10,000 cP, or above 100,000 cP. In certain embodiments, the viscosity of the composition at 25° C. is about 100 cP to about 50,000 cP, about 1,000 cP to about 30,000 cP, or about 2,000 cP to about 20,000 cP. In certain embodiments, the viscosity of the composition at 25° C. is about 1,000 cP to about 500,000 cP, about 10,000 cP to about 300,000 cP, or about 30,000 cP to about 100,000 cP. Each possibility represents a separate embodiment of the invention.

The size of the ACC particles in the compositions of the present invention may be determined directly or indirectly by several methods known in the art. In certain embodiments, the particles may be spherical, and their longest dimension is their diameter. In certain embodiments, the particles may be elongated, and their longest dimension is their elongated or longest axis.

An "average" particle size of a plurality of particles may be defined and therefore calculated by several methods known in the art. Mean, median, and mode are the three most common kinds of "averages". The "mean" (or arithmetic mean) is the sum of a collection of values divided by the number of values in the collection. The "median" is the value separating the higher half of a collection of values from the lower half. The "mode" is the value, or a range of values, that appears most often in a collection of values.

In certain embodiments, the ACC particles are having an average particle size of their longest dimension of about 0.1 µm to about 1000 µm, about 0.1 µm to about 100 µm, or about 0.1 µm to about 10 µm. In certain embodiments, the ACC particles are having an average particle size of their longest dimension of below 1000 µm, below 100 µm, or below 10 µm. Each possibility represents a separate embodiment of the invention. Large particles may be agglomerates of smaller particles, such as for examples grains of 1 to 10 µm in size. According to other embodiments, the composition is essentially devoid of agglomerates. It is to be understood that the dimensions refer to the dimensions of the particles introduced into the composition, and that in suspension agglomerates may form that have larger dimensions.

Although the compositions provided by the present invention are substantially non-aqueous during manufacture, storage and use, certain water content may not be completely avoided. In certain embodiments, the compositions of the present invention comprise less than about 20% by weight water of the total composition. In certain embodiments, the compositions of the present invention comprise less than about 5% by weight water of the total composition. In certain embodiments, the compositions of the present invention comprise less than about 1% by weight water of the total composition.

In certain embodiments, the compositions of the present invention comprise at least about 0.01%, at least about 0.1%, or at least about 1% by weight ACC of the total composition. In certain embodiments, the compositions of the present invention comprise about 0.01 to about 40%, about 0.01 to about 10%, about 0.1 to about 10%, about 1 to about 10%, or about 5 to about 20% by weight ACC of the total composition. Each possibility represents a separate embodiment of the invention. According to the principles of the present invention, other cosmeceutical or pharmaceutical agents may be further comprised in the compositions provided by the present invention, in the ACC particle and/or in the liquid carrier.

In certain embodiments, the non-aqueous liquid carrier is selected from the group consisting of organic polyols, water-immiscible lipids, synthetic oils, and mixtures thereof. In certain embodiments, the non-aqueous liquid carrier comprises an organic polyol, a water-immiscible lipid, a synthetic oil, or any combination thereof. Each possibility represents a separate embodiment of the invention.

The term "organic polyol" as used herein includes any organic substance containing multiple hydroxyl groups. The term "water-immiscible lipid" as used herein includes any lipid which is water-immiscible. Miscibility of two materials is often determined optically: when two miscible materials are combined, the resulting liquid is clear. If the mixture is cloudy the two materials are immiscible. Other methods for determining miscibility are well known in the art. The term "synthetic oil" as used herein includes artificially-made oils, such as silicone-based synthetic oil.

According to some embodiments, the silicone-based liquid is a polydiorganosiloxane. The polydiorganosiloxane may be a linear, cyclic or cross-linked polydiorganosiloxane. The polydiorganosiloxane can be selected from polydimethylsiloxane, known also as "silicone" and "dimethicone", polyphenylmethylsiloxane, diphenylsiloxane-dimethylsiloxane copolymer, dimethylsiloxane-methylvinylsiloxane copolymer, dimethylsiloxane-phenylmethylsiloxane copolymer, and diphenylsiloxane-dimethylsiloxane-methylvinylsiloxane copolymer.

In some embodiments, the silicon-bases liquid includes a synthetic oil. In further embodiments, the oil includes a silicone oil. The term "silicone oil" may refer to any liquid polymerized siloxane with organic side chains, mostly to polydimethylsiloxane. According to some embodiments, the silicone oil is selected from dimethylsilicone, phenylsilicone, phenyltrimethicone, diphynyldimethicone or polymethylphenylsiloxane.

Preferred polyols are selected from diols, triols and combinations thereof. According to some embodiments, the polyol is a diol. The term "diol", as used herein, refers to a chemical compound containing two hydroxyl groups per molecule. A non-limiting example of a low-molecular weight diol includes propylene glycol. According to some embodiments, the polyol is a triol. The term "triol", as used herein, refers to a chemical compound containing three hydroxyl groups per molecule. A non-limiting example of a low-molecular weight triol includes glycerol (also termed herein "glycerin").

Examples of high molecular weight polyols may include polyether polyols, polyester polyols, polycarbonate polyols, polyvinylalcohol, polysiloxane polyols, halogenated polyethers and polyesters, and the like, and any mixtures or combinations thereof. Polyether polyols include any compound containing —C—O—C— group and C—OH group. The non-limiting example of polyether polyol useful in the compositions of the present invention includes polyethylene glycol (PEG). According to some embodiments, molecular weight of PEG is in the range of 100-600 Da., such as 200-500 Da., or 300-400 Da. Polyester polyols include any compound containing —C(O)—O— group and C—O group. Polycarbonate polyols include any compound containing —O—C(=O)—O— group and C—OH group.

In certain embodiments, the organic polyol is selected from the group consisting of propylene glycol (PG), a polyethylene glycol (PEG), a PEG derivative, glycerol, and any combination thereof. In certain embodiments, the organic polyol is selected from the group consisting of propylene glycol (PG), a polyethylene glycol (PEG), a PEG derivative, and any combination thereof. In certain embodiments, the PEG is selected from the group consisting of PEG 100, PEG 200, PEG 300, PEG 400, PEG 500, PEG 600, PEG 700, PEG 800, PEG 900, and any combination thereof, wherein the number refers to the molecular weight of the polymer. In certain embodiments, the PEG is selected from the group consisting of a "branched" PEG having 3-10 PEG chains emanating from a central core group, a "star" PEG having 10-100 PEG chains emanating from a central core group, and a "comb" PEG having multiple PEG chains linked to a polymer backbone. Each possibility represents a separate embodiment of the invention.

The term "PEG derivative" means an ethylene glycol derivative having the common repeating unit of PEG. Examples of PEG derivatives include, but are not limited to, diethylene glycol (DEG), tetraethylene glycol (TEG), polyethylene glycol having primary amino groups, di(ethylene glycol) mono allyl ether, di(ethylene glycol) mono tosylate, tri(ethylene glycol) mono allyl ether, tri(ethylene glycol) mono tosylate, tri(ethylene glycol) mono benzyl ether, tri (ethylene glycol) mono trityl ether, tri(ethylene glycol) mono chloro mono methyl ether, tri(ethylene glycol) mono tosyl mono allyl ether, tri(ethylene glycol) mono allyl mono methyl ether, tetra(ethylene glycol) mono allyl ether, tetra (ethylene glycol) mono methyl ether, tetra(ethylene glycol) mono tosyl mono allyl ether, tetra(ethylene glycol) mono tosylate, tetra(ethylene glycol) mono benzyl ether, tetra (ethylene glycol) mono trityl ether, tetra(ethylene glycol) mono 1-hexenyl ether, tetra(ethylene glycol) mono 1-heptenyl ether, tetra(ethylene glycol) mono 1-octenyl ether, tetra(ethylene glycol) mono 1-decenyl ether, tetra(ethylene glycol) mono 1-undecenyl ether, penta(ethylene glycol) mono methyl ether, penta(ethylene glycol) mono allyl mono methyl ether, penta(ethylene glycol) mono tosyl mono methyl ether, penta(ethylene glycol) mono tosyl mono allyl ether, hexa(ethylene glycol) mono allyl ether, hexa(ethylene glycol) mono methyl ether, hexa(ethylene glycol) mono benzyl ether, hexa(ethylene glycol) mono trityl ether, hexa (ethylene glycol) mono 1-hexenyl ether, hexa(ethylene glycol) mono 1-heptenyl ether, hexa(ethylene glycol) mono 1-octenyl ether, hexa(ethylene glycol) mono 1-decenyl ether, hexa(ethylene glycol) mono 1-undecenyl ether, hexa (ethylene glycol) mono 4-benzophenonyl mono 1-undecenyl ether, hepta(ethylene glycol) mono ally! ether, hepta(ethylene glycol) mono methyl ether, hepta(ethylene glycol) mono tosyl mono methyl ether, hepta(ethylene glycol) monoallyl mono methyl ether, octa(ethylene glycol) mono allyl ether, octa(ethylene glycol) mono tosylate, octa(ethylene glycol) mono tosyl mono allyl ether, undeca(ethylene glycol) mono methyl ether, undeca(ethylene glycol) mono allyl mono methyl ether, undeca(ethylene glycol) mono tosyl mono methyl ether, undeca(ethylene glycol) mono allyl ether, octadeca(ethylene glycol) mono allyl ether, octa(ethylene glycol), deca(ethylene glycol), dodeca(ethylene glycol), tetradeca(ethylene glycol), hexadeca(ethylene glycol), octadeca(ethylene glycol), benzophenone-4-hexa(ethylene glycol) allyl ether, benzophenone-4-hexa(ethylene glycol) hexenyl ether, benzophenone-4-hexa(ethylene glycol) octenyl ether, benzophenone-4-hexa(ethylene glycol) decenyl ether, benzophenone-4-hexa(ethylene glycol) undecenyl ether, 4-flourobenzophenone-4'-hexa(ethylene glycol) allyl ether, 4-flourobenzophenone-4λ-hexa(ethylene glycol) undecenyl ether, 4-hydroxybenzophenone-4'-hexa(ethylene glycol) allyl ether, 4-hydroxybenzophenone-4λ-hexa(ethylene glycol) undecenyl ether, 4-hydroxybenzophenone-4"-tetra(ethylene glycol) allyl ether, 4-hydroxybenzophenone-4"-tetra (ethylene glycol) undecenyl ether, 4-morpholinobenzophenone-4r-hexa(ethylene glycol) allyl ether, 4-morpholinoberizophenone-4λ-hexa(ethylene glycol) undecenyl ether, 4-morpholinobenzophenone-4Metra (ethylene glycol) allyl ether, and 4-morpholinobenzophenone-4r-tetra(ethylene glycol) undecenyl ether.

In some embodiments, the composition may comprise about 5-99.95% w/w polyol. In some embodiments, the composition comprises about 50-99.95% w/w polyol or about 5-95% w/w polyol. In certain embodiments, the composition comprises about 9, 10, 11, 33, 35, 61, 70, 77, 88, 89, 91, 98 or 99% w/w. Each possibility represents a separate embodiment of the invention.

The term "medium-chain triglycerides (MCTs)", as used herein, refers to triglycerides whose fatty acids have an aliphatic tail of 6-12 carbon atoms. The fatty acids found in MCTs are called medium-chain fatty acids (MCFAs). Medium-chain triglycerides are composed of a glycerol backbone and three fatty acids, wherein two or three of the fatty acid chains attached to glycerol are medium-chain in length. The medium-chain fatty acids of the MCTs include caproic acid (C6:0), caprylic acid (C8:0), capric acid (C10:0), and lauric acid (C12:0). According to certain embodiments, the liquid formulation includes caprylic/capric triglyceride. Rich sources for commercial extraction of beneficial MCTs include coconut oil and palm seed oil.

In certain embodiments, the water-immiscible lipid is selected from the group consisting of a natural oil, a medium-chain triglyceride, and any combination thereof. In certain embodiments, the natural oil is selected from the group consisting of castor oil, corn oil, cottonseed oil, olive oil, peanut oil, peppermint oil, sunflower oil, sesame oil, soybean oil, hydrogenated vegetable oils, hydrogenated soybean oil, and combinations thereof. In certain embodiments, the medium-chain triglyceride comprises medium-chain triglycerides of coconut oil or palm seed oil. In certain embodiments, the natural oil is a glyceride. In certain embodiments, the glyceride is hydrogenated. In certain embodiments, the glyceride is selected from a mono-, di- or tri-glyceride. In certain embodiments, the glyceride is a long chain glyceride.

The term "natural oil" as used herein refers to any oil obtained from, or identical to an oil obtained from, a natural origin, such as a plant or vegetable.

In certain embodiments, the synthetic oil is a silicone oil. In certain embodiments, the synthetic oil is selected from the group consisting of cyclopentasiloxane, dimethiconol, cetyl dimethicone, caprylyl methicone, $C_{30-45}$ alkyl methicone, phenyl trimethicone, dimethicone crosspolymer, vinyl dimethicone crosspolymer, peg/ppg-18/18 dimethicone, and PEG-12 dimethicone.

In certain embodiments, the synthetic oil is selected from the group consisting of a polydimethylsiloxane, a functionally modified dimethylsiloxane, a polydimethylsiloxane-copolyol, a polydimethylsiloxane-crosspolymer, and combinations thereof. In certain embodiments, the polydimethylsiloxane is linear. In certain embodiments, the polydimethylsiloxane is cyclic. In certain embodiments, the polydimethylsiloxane is selected from the group consisting of a cyclopentasiloxane, a cyclotetrasiloxane, and combinations thereof. In certain embodiments, the functionally modified dimethylsiloxane is a siloxane monomer modified by independently replacing one or two methyl groups with an H, OH, phenyl, propyl, octyl, amino-propyl, or vinyl. In certain embodiments, the polydimethylsiloxane-copolyol is cyclopentasiloxane and a mixture of PEG/PPG-18/18 dimethicone. In certain embodiments, the polydimethylsiloxane-crosspolymer is a cyclopentasiloxane and a mixture of dimethicone crosspolymer. Each possibility represents a separate embodiment of the invention. The polydimethylsiloxane can be selected from linear, cyclic and cross-linked polydimethylsiloxanes.

The term "functionally modified dimethylsiloxane" as used herein refers to any compound produced by replacing at least one methyl group of dimethylsiloxane with a different group.

In certain embodiments, the compositions provided by the present invention further comprise at least one excipient selected from the group consisting of a surfactant, an emollient, a thickening agent and a dispersing agent.

As used herein, the term "surfactant" is defined as a compound that lowers the surface tension (or interfacial tension) between two liquids or between a liquid and a solid. Surfactants may act as detergents, wetting agents, emulsifiers, foaming agents, and dispersants. As used herein, the term "emulsifier" or "emulsifying agent" is defined as an agent that forms or preserves an emulsion and prevents or reduces separation of two 2 immiscible liquids. Without wishing to being bound by theory or mechanism of action, the surfactant is added to the composition to improve the uniformity of the dispersion of the sACC in the liquid carrier.

According to some embodiments, the surfactant prevents or reduces floating or sedimentation of the sACC particles in the dispersing vehicle. The surfactant may further prevent or reduce agglomeration of the sACC particles. The surfactant may comprise a non-ionic, cationic, anionic, amphoteric surfactant or combinations thereof. According to some embodiments, the liquid formulation comprises at least two different types of surfactants.

As used herein, the term "emollient" is defined as a compound or a mixture of compounds that make the external layers of the skin (epidermis) softer and more pliable. Emollients increase the skin's hydration (water content) e.g. by reducing evaporation.

As used herein, the term "thickening agent" is defined as a compound that can increase the viscosity of a liquid without substantially changing its other properties. Thickeners may also improve the suspension of other ingredients or emulsions which increases the stability of the product.

As used herein, the term "dispersing agent" is defined as a compound that improves the separation of particles and/or prevents or ameliorates settling or clumping of the particles. Without wishing to being bound by theory or mechanism of action, the dispersing agent is added to the liquid formulation to improve the uniformity of the dispersion of the ACC in the dispersing vehicle. According to some embodiments, the dispersing agent prevents or reduces floating or sedimentation of the sACC particles in the dispersing vehicle. The dispersing agent may further prevent or reduce agglomeration of the ACC particles. The dispersing agent may include a solubilizing agent.

The dispersing agent can be selected from the group consisting of biopolymers, biocompatible polymers and combinations thereof.

According to some embodiments, the biopolymer comprises a cyclodextrin. The cyclodextrin can be selected from $\alpha$-, $\beta$- or $\gamma$-cyclodextrin or a pharmaceutically acceptable derivative thereof, such as, for example, a hydroxypropyl cyclodextrin or sulfobutylether cyclodextrin. Each possibility represents a separate embodiment of the invention. Optionally, the biopolymer may comprise a protein. A non-limiting example of a protein useful in the formulations of the present invention includes human serum albumin.

The biocompatible polymer suitable for use as a dispersing agent in the liquid formulations of the present invention may be biodegradable or non-biodegradable. The non-limiting examples of a biocompatible non-biodegradable polymer include polyvinyl alcohol (PVA) and polyvinylpyrrolidone. The biodegradable polymer may comprise a polyester, such as, for example a polylactic acid, polyglycolic acid, a poly(lactic-co-glycolic acid), or poly phospholipids.

Non-limiting examples of possible non-ionic organic surfactants include polysorbates, such as polyoxyethylene sorbitan monolaurate (Tween 20), polyoxyethylene sorbitan monopalmitate (Tween 40), polyoxyethylene sorbitan monostearate (Tween 60) and polyoxyethylene sorbitan monooleate (Tween 80); glyceryl stearate, such as Cutina GMS V; polyoxyethylene (POE) fatty acid esters, such as Myrj 45, Myrj 49, Myrj 52 and Myrj 59; sorbitan fatty acid esters, such as sorbitan monolaurate (Span 20), sorbitan monopalmitate (Span 40), sorbitan monooleate (Span 80), sorbitan monostearate (Span 60); mono/diglycerides of octanoic/dectanoic acids, such as but not limited to Imwitor-742, Imwitor-308; poly(oxyethylene) alkylyl ethers, such as poly(oxyethylene) cetyl ether (Brij 52, Brij 56, Brij 58), poly(oxyethylene) palmityl ether, polyethylene oxide hexadecyl ether, polyethylene glycol cetyl ether, and the like; polyethoxylene castor oil derivatives, such as Cremophor EL, ELP and RH 40; PEG-6 octanoic/decanoic glycerides, such as Softigen 767 and the like; polyoxyethylene glycerol trioleate, such as but not limited to Tagat TO; decaglycerol mono/dioleate, such as Caprol PGE860 and the like; sucrose esters of fatty acids, such as but not limited to a sucrose ester of palm oil and Sisterna SP10; poloxamers, which are nonionic triblock copolymers composed of a central hydrophobic chain of polyoxypropylene (poly(propylene oxide)) flanked by two hydrophilic chains of polyoxyethylene (poly (ethylene oxide)), also known by the trade names Synperonics, Pluronics, Kolliphor, and Solutol; and a combination thereof. Each possibility represents a separate embodiment of the invention.

Non-limiting examples of possible cationic surfactants include phosphatides, such as phosphatidyl choline and the like; quaternary ammonium cationic surfactants, such as hexadecyltrimethyl ammonium bromide and the like; pyrimidinium cationic surfactants, such as, but not limited to dodecyl pyridinium chloride; and a combination thereof.

The anionic surfactants useful in the preparation of the liquid formulations of stabilized ACC include sodium alkyl sulfates, such as, but not limited to sodium lauryl sulfate; sodium alkyl sulfonates; sodium alkyl aryl sulfonates, such as sodium dodecyl benzene sulfonate and the like; sodium stearate; dioctyl sodium sulfosuccinate; sodium cholate; and combinations thereof. Each possibility represents a separate embodiment of the invention.

The amphoteric surfactant may include lecithin, N-dodecyl alanine, cocamidopropyl amino betaine or a combination thereof. Each possibility represents a separate embodiment of the invention.

In certain embodiments, the surfactant is a non-ionic organic surfactant or an anionic organic surfactant. In certain embodiments, the non-ionic organic surfactant is selected from the group consisting of polysorbates, sorbitan esters, fatty acid esters, wax esters, poloxamers, and phospholipids. In certain embodiments, the polysorbates are selected from the group consisting of Tween 80, Tween 60, Tween 40, Tween 20, and combinations thereof. In certain embodiments, the fatty acid esters are selected from the group consisting of polyoxyethylene fatty acid esters, sucrose esters of fatty acids, glycerol monostearate, and combinations thereof. In certain embodiments, the fatty acid esters are selected from the group consisting of Span 80, Span 60, Span 40, Span 20, Sisterna, Cutina, MYRJ 52, solutol HS15, ethyl oleate, ethyl palmitate, ethyl myristate, ethyl stearate, and combinations thereof. In certain embodiments, the wax ester is isostearyl isostearate. In certain embodiments, the anionic organic surfactant is sodium lauryl sulfate. Each possibility represents a separate embodiment of the invention.

In certain embodiments, the emollient is selected from the group consisting of a wax, a solid fat, a glyceride, an ethoxylated fatty alcohol, and combinations thereof.

In certain embodiments, the thickening agent is selected from the group consisting of a cellulose polymer, silsesquioxane, silica, and combinations thereof. In certain embodiments, the cellulose polymer is selected from the group consisting of hydroxypropylethylcellulose, sodium carboxymethyl cellulose, and combinations thereof. Each possibility represents a separate embodiment of the invention.

In certain embodiments, the dispersing agent is a cyclodextrin. In certain embodiments, the cyclodextrin is selected from the group consisting of α-cyclodextrin, β-cyclodextrin, γ-cyclodextrin, and combinations thereof. Each possibility represents a separate embodiment of the invention.

A stabilizer suitable for stabilization of ACC may be selected from, but not limited to, organic acids; phosphoric or sulfuric esters of hydroxyl carboxylic acids; organoamine compounds including amino acids; hydroxyl bearing organic compounds, including carbohydrates; organophosphorous compounds or salts thereof; organophosphates, organophosphonates; inorganic phosphorous acids; polyphosphates; bio-essential inorganic ions; or combinations thereof, provided that the selected one or more stabilizer are food grade. Optionally, the stabilizer may comprise a molecule having one or more functional groups selected from, but not limited to, hydroxyl, carboxyl, ester, amine, phosphino, phosphono, phosphate, sulfonyl, or sulfino groups. The hydroxy bearing compounds, combined with the hydroxide, optionally also bear other functions like carboxyl, etc. but with the hydroxyl not being esterified. The organic acids may comprise, for example, ascorbic acid or acetic acid, and optionally they include carboxylic acids having at least two carboxylic groups and molecular weight not larger than 250 g/mol, such as citric acid, tartaric acid, malic acid, etc. The organic acid may further include oxalic acid, malonic acid, glutaconic acid, succinic acid, maleic acid, lactic acid, aconitic acid or combinations thereof.

The esters may include, for example, phosphoenolpyruvate. In another embodiment, the phosphoric or sulfuric esters of hydroxyl carboxylic acids comprise amino acids, examples of which include phosphoserine, phosphothreonine, sulfoserine, and sulfothreonine. In another embodiment, the stabilizing molecule is a phosphate ester derivative of an amino acid, such as phosphocreatine. The hydroxyl bearing compounds combined with hydroxide may comprise, for example, mono-, di-tri-, oligo-, and polysaccharides like sucrose or other polyols like glycerol. The hydroxyl bearing compounds may further comprise hydroxy acids like citric acid, tartaric acid, malic acid, etc., or hydroxyl-bearing amino acids such as serine or threonine. Each possibility represents a separate embodiment of the present invention.

The non-limiting examples of stabilizers containing phosphate, phosphite, phosphonate groups and salts or esters thereof include phytic acid, dimethyl phosphate, trimethyl phosphate, sodium pyrophosphate, tetraethyl pyrophosphate, ribulose bisphosphate, etidronic acid, zoledronic acid and other medical bisphosphonates, 3-phosphoglyceric acid salt, glyceraldehyde 3-phosphate, 1-deoxy-D-xylulose-5-phosphate sodium salt, diethylene triamine pentakis(methylphosphonic acid), nitrilotri(methylphosphonic acid), 5-phospho-D-ribose 1-diphosphate pentasodium salt, adenosine 5'-diphosphate sodium salt, adenosine 5'-triphosphate disodium salt hydrate, α-D-galactosamine 1-phosphate, 2-phospho-L-ascorbic acid trisodium salt, α-D-galactose 1-phosphate dipotassium salt pentahydrate, α-D-galactosamine 1-phosphate, O-phosphorylethanolamine, disodium salt hydrate, 2,3-diphospho-D-glyceric acid pentasodium salt, phospho(enol)pyruvic acid monosodium salt hydrate, D-glyceraldehyde 3-phosphate, sn-glycerol 3-phosphate lithium salt, D-(−)-3-phosphoglyceric acid disodium salt, D-glucose 6-phosphate sodium salt, phosphatidic acid, ibandronate sodium salt, phosphonoacetic acid, DL-2-amino-3-phosphonopropionic acid or combinations thereof.

The bio-essential inorganic ions may include, inter alia, Na, K, Mg, Zn, Fe, P, S, N; P or S in the phase of oxides; or N as ammonia or nitro groups.

Further examples for stabilized ACC and the preparation thereof may be found in International Patent Applications Nos. WO 2009/053967 and WO 2014/024191, which are hereby incorporated by reference in their entirety.

In certain embodiments, the at least one ACC stabilizing agent is selected from the group consisting of an organic acid, a sulfuric ester of a hydroxyl carboxylic acid, a sulfuric ester of a hydroxyl carboxylic acid, an organoamine compound, an organic compound comprising a hydroxyl, an organophosphorous compound or a salt thereof, a bisphosphonate compound, an organophosphate compound, an organophosphonate compound, an inorganic phosphorous acid, an organic or inorganic polyphosphate compound, an organic polyphosphate such as ATP and phytic acid, an organic surfactant, a bio-essential inorganic ion, and any combination thereof. Each possibility represents a separate embodiment of the invention.

According to some specific embodiments, the at least one stabilizer of the stabilized ACC is selected from the group consisting of organic acids; phosphoric or sulfuric esters of hydroxyl carboxylic acids; organoamine compounds including amino acids; hydroxyl bearing organic compounds, including carbohydrates; organophosphorous compounds or salts thereof; organophosphates, organophosphonates; inorganic phosphorous acids; polyphosphates; bio-essential inorganic ions; and combinations thereof. According to some embodiments, the stabilized ACC comprises at least two stabilizers. In some embodiments, the stabilizers are pharmaceutically acceptable. Some specific unlimited examples of such pharmaceutically acceptable stabilizers include phytic acid, citric acid, sodium pyrophosphate dibasic, Adenosine 5'-monophosphate (AMP) sodium salt, Adenosine 5'-diphosphate (ADP) sodium salt and Adenosine 5'-triphosphate (ATP) disodium salt hydrate, etidronic acid, zoledronic acid, phosphoserine, and other phosphorylated amino acids, and combinations thereof. According to some embodiments, the stabilizer comprises at least one component selected from phosphoric or sulfuric esters of hydroxyl carboxylic acids, such as phosphoenolpyruvate, phosphoserine, phosphothreonine, sulfoserine or sulfothreonine and hydroxyl bearing organic compounds, selected from mono-, di-, tri-, oligo- and poly-saccharides, for example, sucrose, mannose, glucose. The hydroxyl bearing compound may further comprise at least one alkali hydroxide, such as sodium hydroxide, potassium hydroxide and the like. The phosphorylated acids may be present in oligopeptides and polypeptides. In other embodiments of the invention, the stabilizer is an organic acid, preferably a carboxylic acid, including a monocarboxylic acid, dicarboxylic acid or tricarboxylic acid. Each possibility represents a separate embodiment of the invention. The organic acid is preferably selected from the group consisting of citric acid, oxalic acid, malonic acid, glutaconic acid, succinic acid, tartaric acid, maleic acid, lactic acid, aconitic acid, malic acid and combinations thereof. In some embodiments of the invention, the stabilizer is selected from phosphorylated amino acids, polyols and combinations thereof. In some embodiments, the stabilized ACC comprises a stabilizer comprising of a carboxylic acid or multiple carboxylic acids. In some embodiments, the stabilized ACC comprises a phosphorylated compound as a stabilizer wherein the phosphorylation is performed on the hydroxyl group of an organic compound. In some embodiments, the stabilized ACC comprises a stabilizer selected from the group consisting of citric acid, phosphoserine, phosphothreonine and combinations thereof. In certain embodiments, the stabilized ACC comprises citric acid. According to some embodiments, the stabilized ACC is derived from a crustacean gastrolith. In some embodiments, the stabilizer constitutes from about 0.1 to about 15% wt. of the total weight of the stabilized ACC. According to other embodiments, ACC is stabilized by the dispersing vehicle of the non-aqueous semi-solid formulation.

According to some embodiments, the composition retains at least 90% of calcium carbonate in the amorphous state thereof for at least 1 month, at least 2 months, at least 3 months, at least 4 months, at least 5 months, or at least 6 month at ambient temperature. Each possibility represents a separate embodiment of the invention.

According to some embodiments, the liquid carrier comprises a polyol and a water-insoluble lipid. According to further embodiments, the polyol forms a continuous phase and the water-insoluble lipid forms a dispersed phase of the emulsion. Optionally, the polyol forms a dispersed phase and the water-insoluble lipid forms a continuous phase of the emulsion. According to some embodiments, the stabilized ACC is dispersed in said emulsion. The stabilized ACC can be dispersed in the continuous phase of the emulsion or in the dispersed phase of the emulsion. Each possibility represents a separate embodiment of the invention.

According to some embodiments, the liquid carrier further comprises a dispersing agent. The dispersing agent can be used to assist and maintain homogeneous distribution of the ACC particles throughout the liquid carrier. The dispersing agent may be a solubilizing agent. The dispersing agent can be selected from the group consisting of biopolymers, biocompatible polymers, and combinations thereof. According to some embodiments, the biopolymer comprises a cyclodextrin. Optionally, the biopolymer can be a protein. According to some embodiments, the biopolymer is human serum albumin. The biocompatible polymer can be selected from the group consisting of polyester, polyvinyl alcohol (PVA), polyvinylpyrrolidone and combinations thereof. Each possibility represents a separate embodiment of the invention. In some embodiments, the polyester is selected from polylactic acid, polyglycolic acid, poly(lactic-co-glycolic acid) or combinations thereof. In some embodiments, the protein comprises human serum albumin.

According to some embodiments, the liquid carrier further comprises at least one surfactant. The surfactant can be selected from the group consisting of polysorbates, sorbitan esters, fatty acid esters, poloxamers, phospholipids, silicone based emulsifiers, and combinations thereof. The fatty acid esters can be selected from polyoxyethylene fatty acid esters, sucrose esters of fatty acids, glycerol esters of fatty acids and combinations thereof. The non-limiting example of a suitable glycerol ester of fatty acid is glycerol monostearate. The non-limiting example of a suitable phospholipid is lecithin. Each possibility represents a separate embodiment of the invention.

According to some embodiments, the liquid carrier is highly viscous ("semi solid") and comprises about 0.01-10% w/w stabilized ACC; about 50-99.95% w/w organic liquid, silicone-based liquid or a combination thereof; and about 0.1-25% w/w dispersing agent. According to some embodiments, the liquid formulation comprises about 0.1-10% w/w stabilized ACC; about 5-99.95% w/w organic liquid, silicone-based liquid or a combination thereof; and about 0.1-30% w/w surfactant. Optionally, the liquid composition can comprise about 0.01-20% w/w stabilized ACC; about 50-99.95% w/w organic liquid, silicone-based liquid or a combination thereof; about 0.1-25% w/w dispersing agent; and about 0.1-2.5% w/w surfactant.

According to certain embodiments, the liquid carrier is in a form of a suspension, wherein the liquid carrier comprises at least one organic liquid comprising a polyol. In further embodiments, the polyol comprises a combination of propylene glycol and PEG. The liquid carrier can further include a dispersing agent and optionally include a surfactant. In certain such embodiments, the liquid carrier comprises about 0.01-20% w/w stabilized ACC; about 50-99.95% w/w polyol; and about 0.1-25% w/w dispersing agent. According to further embodiments, the liquid carrier comprises about 0.01-4% w/w stabilized ACC; about 75-99.95% w/w polyol; and about 0.1-25% w/w dispersing agent.

According to certain embodiments, the liquid carrier is in a form of an emulsion, wherein the liquid carrier comprises at least two organic liquids comprising a polyol and a water-insoluble lipid. In certain such embodiments, the composition comprises about 0.01-10% w/w stabilized ACC; about 5-95% w/w polyol; about 0.1-40% w/w water-insoluble lipid; and about 0.1-75% w/w surfactant. According to further embodiments, the composition comprises about 0.1-10% w/w stabilized ACC; about 5-80% w/w polyol; about 15-40% w/w water-insoluble lipid; and about 0.1-40% w/w surfactant.

According to some embodiments, the composition further comprise at least one silicone-based liquid. According to certain embodiments, the liquid carrier comprises about 0.1-20% w/w stable ACC; about 0.1-20% w/w polyol; about 5-70% silicone-based liquid; about 0.1-20% w/w water-insoluble lipid; and about 1-40% w/w surfactant.

In some embodiments, the composition retains at least 90% of the total weight of the stabilized ACC in the amorphous form thereof for at least 6 months, in ambient temperature. In some preferred embodiments, the ACC, which retains the amorphous phase thereof, is an undissolved ACC. The solubility of the stabilized ACC in the liquid carrier may be less than about 1% w/w, such as less than about 0.5% w/w or less than about 0.1% w/w. Each possibility represents a separate embodiment of the invention.

In some embodiments, the composition comprises stabilized ACC, polyol and dispersing agent. In further embodiments, the composition comprises stabilized ACC, polyol, dispersing agent and a surfactant.

In some embodiments, the composition comprises 0.01-20% w/w stabilized ACC, 50-99.95% w/w polyol and 0.1-25% w/w dispersing agent. In further embodiments, the composition comprises 0.01-4% w/w stabilized ACC, 75-99.95% w/w polyol and 0.1-25% w/w dispersing agent. In still further embodiments, the composition comprises 0.01-20% w/w stabilized ACC, 50-99.95% w/w polyol, 0.1-25% w/w dispersing agent and 0.1-2.5% w/w surfactant. In yet further embodiments, the composition comprises 0.01-4% w/w stabilized ACC, 75-99.95% w/w polyol, 0.1-25% w/w dispersing agent and 0.1-2.5% w/w surfactant.

In some embodiments, the composition comprises 0.01-2% w/w stabilized ACC, 40-80% w/w propylene glycol, 20-60% PEG, and 0.1-15% w/w cyclodextrin. In further embodiments, the composition comprises 0.01-2% w/w stabilized ACC, 40-80% w/w propylene glycol, 20-60% PEG, and 0.1-15% w/w cyclodextrin and 0.1-2.5% w/w poloxamer.

In certain embodiments, the composition comprises about 0.1% w/w stabilized ACC, about 99% w/w polyol and about 0.1% w/w dispersing agent. Optionally, the composition may comprise about 0.05% w/w stabilized ACC, about 99.5% w/w polyol and about 0.5% w/w dispersing agent. Alternatively, the composition may comprise about 0.2% w/w stabilized ACC, about 98% w/w polyol and about 1.5% w/w dispersing agent. In additional embodiments, the composition comprises about 0.8% w/w stabilized ACC, about 89% w/w polyol and about 10% w/w dispersing agent.

In some embodiments, the composition comprises stabilized ACC, polyol, a water-insoluble lipid, and a surfactant. In further embodiments, the composition comprises stabilized ACC, polyol, a water-insoluble lipid, an aromatic alcohol and a surfactant. According to further embodiments, the composition comprises stabilized ACC, propylene glycol, oil, medium chain triglyceride, a phospholipid, a polysorbate and an ethoxylated castor oil derivative. According to some exemplary embodiments, the composition comprises stabilized ACC, PEG, propylene glycol, glycerin, oil, benzyl alcohol, a phospholipid, a polysorbate and a poloxamer. According to some exemplary embodiments, the composition comprises stabilized ACC, PEG, medium chain triglyceride and one or more surfactants.

According to further embodiments, the composition comprises stabilized ACC, PEG, medium chain triglyceride, one or more polysorbates, a sorbitan fatty acid ester, a sucrose fatty acid ester and glyceryl stearate. Optionally, the composition may comprise a stabilized ACC, PEG, medium chain triglyceride, one or more polysorbates, one or more sorbitan fatty acid esters, a polyoxyethylene fatty acid ester and glyceryl stearate.

In some embodiments, the composition comprises 0.01-10% w/w stabilized ACC, 5-95% w/w polyol, 0.1-40% w/w water insoluble lipid and 0.1-75% w/w surfactant. In further embodiments, the composition comprises 0.01-10% w/w stabilized ACC, 5-95% w/w polyol, 0.1-40% w/w water insoluble lipid and 0.1-30% w/w surfactant. In yet further embodiments, the composition comprises 0.1-10% w/w stabilized ACC, 5-80% w/w polyol, 15-40% w/w water insoluble lipid and 0.1-75% w/w surfactant. In some embodiments, the composition comprises 0.01-10% w/w stabilized ACC, 5-95% w/w polyol and 0.1-40% w/w water insoluble lipid, 0.1-30% w/w surfactant and 0.05-1% w/w aromatic alcohol. According to some embodiments, the composition is in a form of a suspension.

In some embodiments, the composition comprises 0.5-10% w/w stabilized ACC, 40-80% w/w propylene glycol, 5-30% w/w oil, 5-30% w/w medium chain triglyceride and 2-15% w/w surfactant. In some embodiments, the composition comprises 0.01-1.5% w/w stabilized ACC, 20-50% w/w propylene glycol, 20-50% w/w propylene glycol, 5-15% w/w glycerin, 5-30% w/w oil and 2-15% w/w surfactant. In further embodiments, the composition comprises 0.01-1.5% w/w stabilized ACC, 20-50% w/w propylene glycol, 20-50% w/w propylene glycol, 5-15% w/w glycerin, 5-30% w/w oil 2-15% w/w surfactant and 0.05-4% benzyl alcohol. In some embodiments, the composition comprises 1-10% w/w stabilized ACC, 5-15% w/w PEG, 15-50% w/w medium chain triglyceride and 25-75% w/w surfactant. In some embodiments, the composition comprises 5-20% w/w stabilized ACC, 20-50% w/w PEG, 10-40% w/w medium chain triglyceride and 25-75% w/w surfactant.

In certain embodiments, the composition comprises about 2% stabilized ACC, about 60% w/w polyol, about 30% w/w water-insoluble lipid and about 7.5% w/w surfactant. Optionally, the composition may comprise about 0.3% stabilized ACC, about 77% w/w polyol, about 15% w/w water-insoluble lipid, about 0.2% w/w aromatic alcohol and about 7.5% w/w surfactant. Alternatively, the composition may comprises about 5% stabilized ACC, about 9% w/w polyol, about 33% w/w water-insoluble lipid and about 52% w/w surfactant. In additional embodiments, the composition comprises about 8% stabilized ACC, about 35% w/w polyol, about 22% w/w water-insoluble lipid and about 48% w/w surfactant.

According to certain embodiments, the composition comprises about 0.1-20% w/w stable ACC; about 0.1-20% w/w polyol; about 5-70% silicone-based liquid; about 0.1-20% w/w water-insoluble lipid; and about 1-40% w/w surfactant.

According to some exemplary embodiments, the composition comprises stabilized ACC, propylene glycol, PEG and cyclodextrin. According to further exemplary embodiments, the composition comprises stabilized ACC, propylene glycol, PEG, poloxamer and cyclodextrin. According to some exemplary embodiments, the composition comprises 0.01-1% stabilized ACC, 40-75% propylene glycol, 30-60% PEG and 0.5-10% cyclodextrin. According to further exemplary embodiments, the composition comprises 0.01-1% stabilized ACC, 40-75% propylene glycol, 30-60% PEG and 0.5-10% cyclodextrin and 0.1-1% poloxamer.

According to some exemplary embodiments, the composition comprises stabilized ACC, PEG, medium chain triglyceride, polysorbate, and fatty acid ester. According to some exemplary embodiments, the composition comprises stabilized 2-10% ACC, 5-15% PEG, 30-40% medium chain triglyceride, 38-48% polysorbate, and 9-13% fatty acid ester. According to some exemplary embodiments, the composition comprises stabilized 5-10% ACC, 30-40% PEG, 15-20% medium chain triglyceride, 15-25% polysorbate, and 15-25% fatty acid ester.

According to some exemplary embodiments, the composition comprises stabilized ACC, propylene glycol, oil, medium chain triglyceride, and one or more surfactants. According to some exemplary embodiments, the composition comprises 1-3% stabilized ACC, 50-70% propylene glycol, 15-20% oil, 10-20% medium chain triglyceride and 5-10% surfactants.

According to some exemplary embodiments, the composition comprises stabilized ACC, PEG, propylene glycol, glycerin, oil, benzyl alcohol and one or more surfactants. According to some exemplary embodiments, the composition comprises 0.1-1% stabilized ACC, 30-40% PEG, 30-40% propylene glycol, 5-15% glycerol, 10-20% oil, 0.1-0.5% benzyl alcohol and 5-10% surfactants.

According to some exemplary embodiments, the composition comprises stabilized ACC, PEG, propylene glycol, cyclodextrin and a cellulose polymer. According to some exemplary embodiments, the composition comprises 1-10% stabilized ACC, 35-45% PEG, 45-55% propylene glycol, 1-5% cyclodextrin and 0.5-3% cellulose polymer.

According to some exemplary embodiments, the composition comprises stabilized ACC, natural oil, propylene glycol, synthetic oil and wax. According to some exemplary embodiments, the composition comprises 1-10% stabilized ACC, 0.5-2% natural oil, 5-15% propylene glycol, 70-80% synthetic oil and 5-15% wax. According to some exemplary embodiments, the composition comprises 1-5% stabilized ACC, 0.5-2% natural oil, 5-15% propylene glycol, 70-80% synthetic oil and 10-15% wax.

According to some exemplary embodiments, the composition comprises stabilized ACC, glycerol, silica, cellulose polymer and surfactant. According to some exemplary embodiments, the composition comprises 1-10% stabilized ACC, 60-80% glycerol, 15-25% silica, 0.5-3% cellulose polymer and 0.5-2% surfactant.

According to some exemplary embodiments, the composition comprises stabilized ACC, PEG, glycerol, and hard fat. According to some exemplary embodiments, the composition comprises stabilized 1-10% stabilized ACC, 20-25% PEG, 5-15% glycerol, and 60-70% hard fat.

According to some embodiments, the composition is selected from Formulations 1-11, presented in Examples 1 to 6, herein below. According to some embodiments, the composition comprises any one of Formulations 1-11, presented in Examples 1 to 6, herein below. According to some embodiments, the composition consists of any one of Formulations 1-11, presented in Examples 1 to 6, herein below.

The present invention further provides, in another aspect, a cosmeceutical composition comprising any one of the compositions described above.

The present invention further provides, in another aspect, a pharmaceutical composition comprising any one of the compositions described above.

The term "cosmeceutical composition" as used herein refers to a composition comprising a combination of cosmetic and pharmaceutical agents. Cosmeceuticals are cosmetic products with biologically active ingredients purporting to have medical or drug-like benefits, particularly in exposed areas of the body, such as the skin. The term "pharmaceutical composition" as used herein refers to a composition comprising a pharmaceutical agent. According to the principles of the present invention, ACC is considered an active pharmaceutical agent. ACC may further be considered as an active cosmetic agent.

In certain embodiments, the pharmaceutical composition comprises ACC and an additional pharmaceutical agent. In certain embodiments, the additional pharmaceutical agent is comprised in the ACC particle. In certain embodiments, the additional pharmaceutical agent is comprised in the liquid carrier.

The term "pharmaceutical composition", as used herein, further includes the compositions according to the principles of the present invention, comprising therapeutically effective amounts of the stabilized ACC, optionally further comprising suitable diluents, preservatives, solubilizers, emulsifiers, adjuvant and/or carriers. A "therapeutically effective amount" as used herein refers to that amount which provides a therapeutic effect for a given condition and administration regimen.

The cosmeceutical or pharmaceutical compositions of the present invention can be administered by various routes of administration, including parenteral, topical, ophthalmic, nasal and oral. In one embodiment, the pharmaceutical composition is administered parenterally, paracancerally, transmucosally, transdermally, intramuscularly, intravenously, intradermally, subcutaneously, intraocularly, intratracheally, intracisternally, intraperitoneally, epidurally, intraventricularly, intracranially or intratumorally.

According to some preferred embodiments, the cosmeceutical or pharmaceutical compositions comprising the ACC compositions according to the principles of the present invention do not require addition of a carrier or diluent. In certain such embodiments, the ACC compositions can be administered in any one of said administration routes without a need for further formulation.

The pharmaceutical composition can be delivered in a controlled release system. For example, the ACC compositions may be administered using intravenous infusion, an implantable osmotic pump, a transdermal patch, liposomes, or other modes of administration.

According to some embodiments, the cosmeceutical or pharmaceutical composition is formulated in a form suitable for parenteral administration. Said form can be selected from a suspension, emulsion or gel. The parenteral administration route may include subcutaneous, intramuscular, intravenous, intradermal, intraocular, intratracheal, intracisternal, intraperitoneal and epidural administration. In certain embodiments, the parenteral administration is intravenous. The cosmeceutical or pharmaceutical compositions formulated for parenteral administration, including intravenous administration, preferably contain no more than 2% w/w stabilized ACC. In certain such embodiments, the stabilized ACC has particles, which mean particle size is less than about 10 μm, less than about 1 μm, or less than about 500 nm. Optionally, the mean particle size of said stabilized ACC is in the range of about 50 nm to about 10 μm.

According to some embodiments, the cosmeceutical or pharmaceutical composition is formulated in a form suitable for topical administration. Said form can be selected from a gel, emulsion, cream, ointment, lotion, paste, suppository or patch. The topical administration route may include epicutaneous, inhalational, ophthalmic, otic or nasal administration. In certain embodiments, the topical administration is ophthalmic. The pharmaceutical composition may be thus formulated in a form of ophthalmic drops or ophthalmic ointment. Each possibility represents a separate embodiment of the invention. The cosmeceutical or pharmaceutical compositions formulated for topical administration, preferably contain about 0.05% to about 10% w/w stabilized ACC. In further embodiments, the mean particle size of said stabilized ACC is in the range of about 100 nm to about 200 µm.

According to some embodiments, the cosmeceutical or pharmaceutical composition is formulated in a form suitable for oral administration. Said form can be selected from a suspension, emulsion, syrup, elixir, capsules or gel. The cosmeceutical or pharmaceutical compositions formulated for oral administration, preferably contain about 1% to about 20% w/w stabilized ACC. In further embodiments, the mean particle size of said stabilized ACC is in the range of about 200 nm to about 1000 µm.

The pharmaceutical compositions comprising the ACC composition according to the principles of the present invention are preferably used in treating conditions associated with calcium metabolism or calcium signaling. Said conditions may be selected from the group consisting of pain, proliferative diseases, neurological disorders, immunologic disorders, cardiovascular diseases, pulmonary diseases, nutritional disorders, reproductive disorders, musculoskeletal disorders, calcium malabsorption and dental problems. Said treating may comprise mitigating the symptoms of the diseases. Said proliferative disease may be selected from sarcomas, carcinomas, lymphomas and melanomas. Said carcinoma is, for example, breast carcinoma or bronchogenic carcinoma. Said treating may lead to shrinking tumors, stopping their growth, or slowing down or inhibiting the cell proliferation in the tumors. Said pain may be selected from postoperative pain, pain after injury, pain associated with cancer, and neuropathic pain. Said neurological disorder may be selected from demyelinating diseases, dementias, and movement disorders; said disorders being, for example, multiple sclerosis, Alzheimer's disease, Parkinson's disease, or other degenerative disease. Said condition to be treated may comprise a bone or bone marrow disorder, such as fracture or osteoporosis. In a preferred embodiment, a composition of the invention is used for treating a neurodegenerative disorder. Calcium malabsorption can exist in patients after bariatric surgery, patients suffering from hypoparathyroidism, Crohn's disease, cystic fibrosis, inflammatory bowel disease or celiac disease. Individuals, consuming additional types of drugs, such as proton pump inhibitors, anticonvulsants, and chronic corticosteroids, may also develop calcium malabsorption.

As used herein, the term "treating" means to ameliorate one or more symptoms associated with the referenced disorder. As used herein, the term "preventing" means to mitigate a symptom of the referenced disorder. As used herein, the phrase "an effective amount" means an amount effective to prevent and/or treat a patient at risk for developing or diagnosed with the referenced disorder, and thus producing the desired therapeutic effect. As used herein, the term "patient" means a mammal (e.g., a human).

According to some embodiments, the cosmeceutical or pharmaceutical composition is formulated in a form suitable for parenteral administration. In certain such embodiments, the composition can be formulated in a form selected from the group consisting of a suspension, gel and emulsion. The parenteral administration can be selected from subcutaneous, intramuscular, subcutaneous, intravenous, intradermal, intraocular, intratracheal, intracisternal, intraperitoneal, or epidural administration. Each possibility represents a separate embodiment of the invention. According to some embodiments, the parenteral administration is intravenous. According to some embodiments, the composition is formulated in an injectable form. In certain such embodiments, the stabilized ACC has particles, wherein the mean particle size is less than about 10 µm, less than about 1 µm, less than about 500 nm, or less than about 100 nm. In further embodiments, the composition comprises up to about 2% w/w stabilized ACC.

According to some embodiments, the cosmeceutical or pharmaceutical composition is formulated in a form suitable for topical administration. In certain such embodiments, the cosmeceutical or pharmaceutical composition is formulated in a form selected from the group consisting of gel, emulsion, cream, ointment, lotion, paste, emulgel (an emulsion in a gel form) suppository and patch.

According to some embodiments, the cosmeceutical or pharmaceutical composition of the present invention provides controllable delivery of the stabilized ACC. According to some embodiments, the cosmeceutical or pharmaceutical composition is formulated in a dosage form of ophthalmic drops.

According to some embodiments, the cosmeceutical or pharmaceutical composition is formulated in a form suitable for oral administration. In certain such embodiments, the cosmeceutical or pharmaceutical composition is formulated in a form selected from the group consisting of suspension, emulsion, syrup, elixir, capsule and gel.

In certain embodiments, the pharmaceutical composition described above is for use in or treating or ameliorating a topical inflammation. In certain embodiments, the pharmaceutical composition described above is for use in treating or ameliorating a skin affliction.

The term "topical inflammation" as used herein refers to any inflammation in exposed areas of the body, such as the skin and in hidden areas such as the oral cavity (including the gum and periodontal pockets), the vagina and the rectum. The term "skin affliction" as used herein refers to any disease, disorder or abnormal condition of the skin, the oral cavity (including the gum and periodontal pockets), the vagina and the rectum.

The present invention further provides, in another aspect, a topical pharmaceutical composition comprising stabilized ACC, formulated for topical administration, for treating or ameliorating a topical inflammation.

The present invention further provides, in another aspect, a topical pharmaceutical composition comprising stabilized ACC, formulated for topical administration, for treating or ameliorating a skin affliction.

In certain embodiments, the inflammation is associated with an auto-immune reaction. In certain embodiments, the skin affliction is psoriasis. In certain embodiments, the skin affliction is psoriasis, and at least one clinical parameter selected from the group consisting of erythema (redness), induration (thickness) and desquamation (scaling) is treated or ameliorated.

The present invention further provides, in another aspect, a method of treating or ameliorating a topical inflammation in a patient in need, comprising the step of topically administering to the patient a therapeutically effective amount of stabilized ACC.

The present invention further provides, in another aspect, a method of treating or ameliorating a skin affliction in a patient in need, comprising the step of topically administering to the patient a therapeutically effective amount of stabilized ACC.

In certain embodiments, the methods described above comprise the step of topically administering to the patient a therapeutically effective amount of any one of the ACC compositions described above.

The present invention further provides, in another aspect, a method of preparing a liquid or semi-solid non-aqueous composition in the form of a dispersion or suspension of amorphous calcium carbonate (ACC) particles, comprising the steps of mixing at least one non-aqueous liquid carrier with at least one additional agent selected from the group consisting of a dispersing agent, a surfactant, a thickening agent and an emollient; and adding ACC to the mixture.

The experiment was repeated with Formulation 1, which contained stabilized ACC having as a stabilizer one or more of pyrophosphate, phosphoserine, etidronic acid, phytic acid, citric acid, ATP, ADP and zoledronic acid. Suspension (Formulation 4) was prepared by a similar method. The surfactant (poloxamer) was added to the suspension in step 2. The composition of Formulation 4 is also presented in Table 1.

TABLE 1

Liquid Formulations of ACC formulated as suspensions (% relates to a weight percent).

| Formulation # | sACC | Liquid carrier #1 | Liquid carrier #2 | Dispersing agent #1 | Dispersing agent #2 | Surfactant |
|---|---|---|---|---|---|---|
| 1 | 0.1% | 45% PG | 53.9% PEG 400 | 1% hydroxypropyl β-cyclodextrin | — | — |
| 2 | 0.05% | 72.5% PG | 26.95% PEG 400 | 0.5% hydroxypropyl β-cyclodextrin | — | — |
| 3 | 0.2% | 44.5% PG | 53.8% PEG 400 | 1.5% hydroxypropyl β-cyclodextrin | — | — |
| 4 | 0.8% | 58.7% PG | 30% PEG 300 | 5% β-cyclodextrin | 5% γ-cyclodextrin | 0.5% poloxamer |

In certain embodiments, the method comprises preparing two separate non-aqueous liquid carriers, wherein the ACC is added to one of the non-aqueous liquid carriers before it is mixed with the other non-aqueous liquid carrier. In certain embodiments, mixing comprises high shear mixing or using a micro-fluidizer. In certain embodiments, mixing continues until all non-liquid agents are dissolved in the non-aqueous liquid carrier. In certain embodiments, the ACC is dry, stabilized ACC. In certain embodiments, the method further comprises heating the non-aqueous liquid carrier.

As used herein, the term "about", when referring to a measurable value such as an amount, a temporal duration, and the like, is meant to encompass variations of +/−10%, or +/−5%, +/−1%, or even +/−0.1% from the specified value.

Having now generally described the invention, the same will be more readily understood through reference to the following examples, which are provided by way of illustration and are not intended to be limiting of the present invention.

Examples

Example 1. Liquid Formulations of ACC Formulated as Suspensions Formulations 1-4

Suspensions (Formulations 1-3, presented in Table 1) were prepared according to the following procedure:

Polyethylene glycol (PEG) and propylene glycol (PG) were mixed in the proportion set forth in Table 1.

Hydroxypropyl beta cyclodextrin was added into the PEG/PG solution with high shear mixing until completely dissolved. Powdered sACC, stabilized with phosphoserine and citric acid, was added to the solution of PEG/PG and hydroxypropyl beta cyclodextrin with high shear mixing until the suspension became transparent. The transparent suspension was mixed in a microfluidizer until reaching a particle size of 100-200 nm. The measured mean particle diameter of the sACC particles in Formulation 1 was found to be lower than 186.2 nm Example 2. Liquid Formulations of ACC Formulated as Emulsions Emulsion (Formulation 5) was prepared according to the following procedure:

The following mixtures were prepared: Phase A mixture, containing PEG 400 (15%), Tween60 (polysorbate) (60%), Tween20 (polyoxyethylene sorbitan monostearate) (6%); Phase B mixture, containing Myritol318 (caprylic/capric triglyceride) (53%), Span60 (sorbitan stearate) (10%), Sisterna SP10C (sucrose polystearate) (5%), Cutina GMS V (glyceryl stearate) (3%), ACC (8%).

Phase A and B (except ACC) were heated separately at approximately 75-80° C. while stirring. The ACC was added slowly to the heated phase B using high shear homogenizer (rotor-stator system) until the ACC powder was completely dispersed. Phase A was slowly added to Phase B using high shear mixing for 5 min. The mixed batch was cooled to room temperature while continuing the mixing with anchor stirrer. Alternative shearing technologies can be used to create the emulsion.

Final composition of Formulation 5 (% refers to a weight percent): PEG 400—9%, Tween 60—38%, Tween 20—4%, Myritol 318—33%, Span 60—6%, Sisterna SP10C—3%, Cutina GMS V—2%, sACC—5%.

Emulsion (Formulation 6) was prepared according to the following procedure:

The following mixtures were prepared: Phase A was prepared containing PEG 400 (42%), ACC (8%), Tween 60 (20%), Span 60 (sorbitan monostearate) (5%), Tween 80 (polyoxyethylene sorbitan monooleate) (5%); Phase B was prepared with Myritol 318 (caprylic/capric triglyceride) (22%), MYRJ52 (polyoxyethylene 40 stearate) (5%), Cutina GMS V (glyceryl stearate) (5%), Span 80 (sorbitan monooleate) (5%), Span 60 (sorbitan monostearate) (3%).

Phases A and B (except ACC) were heated separately to 75-80° C. while stirring. The ACC was added slowly to the heated Phase A using high shear homogenizer (rotor/stator) until ACC powder was completely dispersed. Then, Phase B was slowly added to Phase A using high shear for 5 min. The batch was cooled to room temperature using continuous mixing by anchor stirrer. Other shearing techniques can be used to create the emulsion. As an alternative, ACC may be added at 50° C. after mixing phases A and B.

Final composition of Formulation 6 (% refers to a weight percent): PEG 400—35%, Tween 60—17%, Span 60—7%, Tween 80—4%, Myritol 318—18%, MYRJ52—4%, Cutina GMS V—4%, Span 80—4%, sACC—7%.

Figure 1B:
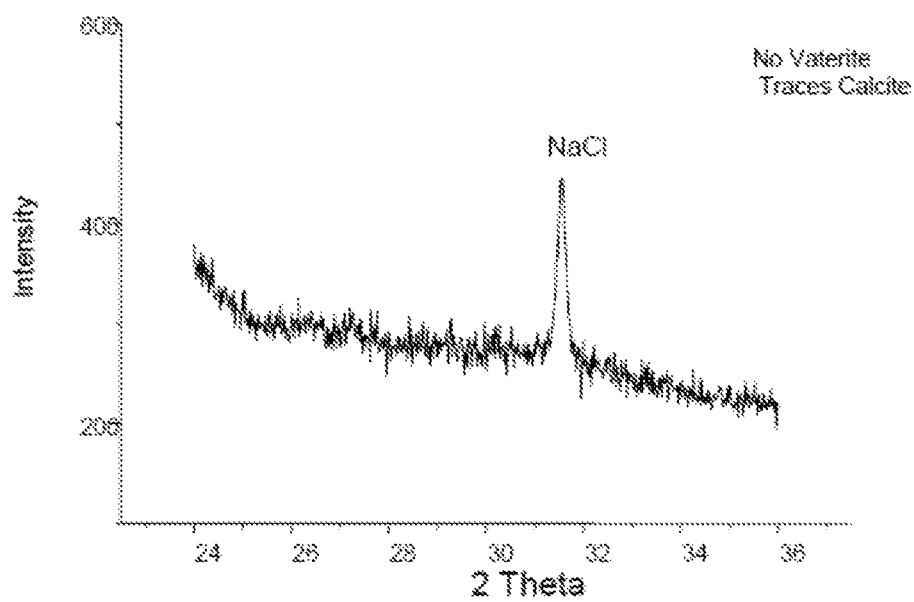
FIG. 1B. XRD pattern of ACC Formulation #6.

Formulations 5 and 6 were analyzed first for their Ca content by atomic absorption (AA) analysis and stability of the ACC in the emulsion was analyzed by Raman and XRD spectroscopies (FIGS. 1A-1B).

Additional emulsions (Formulations 7 and 8) can be prepared by a procedure similar to the one described hereinabove.

Composition of Formulation 7: Propylene glycol—60.6%, Phospholipid—5%, Polyoxyl 35 castor oil—2%, Tween 20—0.4%, injectable oil—15%, caprylic capric triglyceride—15%, sACC—2%.

Composition of Formulation 8: PEG 400 or PEG 300—32%, propylene glycol—35%, glycerin—10%, phospholipid—2%, Tween 80—5%, solutol HS15—0.5%, benzyl alcohol—0.2%, injectable oil—15%, sACC—0.3%.

Example 3. Parenteral Injection of Liquid Formulations of ACC Formulated as Suspensions Laboratory mice were injected via the tail vein with 260-280 µl of a suspension as detailed in Table 2. The mice had no side effects for several days after injection.

TABLE 2

Injection experiment details.

| Mouse | Mouse weight (g) | Formulation # | Injection volume (µl) |
|---|---|---|---|
| Female ICR | 26.7 | 1 | 270 |
| Male black C57 | 27.9 | 1 | 280 |
| Male BALB/c | 25.58 | 1 | 260 |
| Male BALB/c | 27.3 | 1 | 270 |
| Female ICR | 27.2 | 2 | 270 |
| Female ICR | 27.6 | 2 | 280 |
| Male BALB/c | 27 | 3 | 270 |

In repeated experiments with Formulation 1, which was prepared with sACC having as a stabilizer one or more of pyrophosphate, phosphoserine, etidronic acid, phytic acid, citric acid, ATP, ADP and zoledronic acid, Formulation 1 was injected to mice essentially as described above with no detected adverse effects.

Example 4. Use of ACC in the Treatment and Amelioration of Inflammation Formulations 2F, 3F The objective of this study was to assess the potential anti-inflammatory activity of ACC-based formulations, using two routes of administration, in a mouse model of oxazolone-induced contact-delayed-type hypersensitivity.

Animal: ICR female mice in the age of 10 weeks were used for the study.

Animal model: An established animal model of delayed-type hypersensitivity (DTH) as essentially described below was used to test the efficacy of novel anti-inflammatory compounds and formulations. The DTH reaction is an in-vivo model of inflammation driven by cell-mediated immunity. In this model, cutaneous sensitization with oxazolone is used to induce a DTH reaction. Animals are first treated topically with a solution of oxazolone, which derivatizes skin proteins so that they are viewed as foreign by the immune system. This step is termed "sensitization", since thereafter the mouse typically becomes sensitive to re-exposure with oxazolone.

Five/Six days after sensitization, a "challenge" is performed by re-exposure of the mouse to the sensitizing agent oxazolone. Re-exposure to the sensitizing agent results in a release of T-cell cytokines such as IFN-γ and IL-17, which initiate a robust inflammatory response by keratinocytes of the epidermis. The inflammatory response is dependent on T cells, B cells, basophils and activated macrophages.

When re-exposure is performed on an ear of a mouse, the ear typically thickens within a few hours from exposure as a result of the immune response. If left untreated, the ear may reach a maximum thickness within about a day and thereafter reduce in thickness until reaching a near normal value within about 100 hours. Therefore, after a challenge is applied to an ear, the inflammatory response is monitored for a period of 72-96 hours by measuring ear thickness at 24 hour intervals.

Pre-requisites: 31 ICR mice were ethically authorized and allocated for the study: Female, age: 10 weeks, weight: 25-30 gr. ACC based formulations (liquid suspension (cream #1) and cream suspension (cream #2) and ACC oral administration) were prepared by Amorphical. Oxazolone (sigma, storage 4° C.) was used for disease induction.

Sensitization: On study day 1, the abdomen of each mouse was shaved and sensitized by epicutaneous application of 150 µl of 3% oxazolone solution onto the shaved area using a micro-pipettor with disposable tips, as known in the art. After application, the mice were restrained 3 to 5 seconds to allow at least part of the oxazolone solvent to evaporate.

Challenge: On study Day 6, immediately following ear measurement, the right ear was treated topically with 10 µl of 1% oxazolone solution on both sides of the ear (20 µl total).

The treatments for each group are described in the Table below:

TABLE 3

Study Design.

| | | | Treatment | | |
|---|---|---|---|---|---|
| Group # | n | Article | Route | Dose Volume | Duration |
| 1F | 7 | | No applicable - not treated | | |
| 2F | 8 | *Cream # 1 | Topical | ~0.03 ml/animal | Study days 6-10 |
| 3F | 8 | *Cream # 2 | | | |
| 4F | 8 | **ACC oral administration | Feeding | "ad libitum" | Study days 1-10 |

*Cream #1 and cream #2 comprise ACC; preparation procedures and composition are described below.
**ACC oral administration procedure is described below.

Topical liquid suspension 2F: Hydroxypropyl beta cyclodextrin—3%, ACC-PS—5%, PEG400—40%, propylene glycol—50.5%, hydroxypropylethylcellulose—1.5%. Ingredients were mixed with high shear (rotor/stator) mixing for 10 min/speed 3 (HOG-500).

Topical semi solid cream suspension 3F: cyclopentasiloxane & PEG/PPG—18/18 dimethicone—20%, dimethicone & dimethicone crosspolymer—5%, cyclopentasiloxane & cyclotetrasiloxane—48%, beeswax—10%, hydrogenated castor oil—1%, ACC-PS—5%, propylene glycol—11%. All ingredients (except ACC+propylene glycol) were mixed together using magnetic stirrer and heated to 80° C. until homogeneous mix is achieved. Cool down to 50-55° C. ACC was added by using high shear homogenizer for 5 min/speed3. Propylene glycol was added during high shear. Cooled down to room temperature using dissolver mixer.

Oral gavage dosage form: ACC-PS—1%, propylene glycol—99%. Ingredients were mixed with high shear (rotor/stator) mixing for 10 min/speed 3 (HOG-500).

The Creams #1 and #2 for Group 2F and 3F were administered topically on both sides of the right ear commencing on study day 6 (one hour after challenge) until study termination (day 10) spanning a total of 96 hours. The dose volume in all cases was ~0.03 ml/animal Animals from Group 4F were fed ad libitum with ACC on a daily basis commencing on study day 1 and until study termination (Day 10). Test groups were compared to Group 1F that did not receive any treatment neither before nor after the challenge.

Ear thickness measurements were performed using a digital caliper. On study day 6 before challenge (t=0), the thickness of the right ear of each mouse was measured for a baseline value. On study days 7 (24 hours after challenge) up to 10 (96 hours after topical administration) thickness of the right ear was measured to assess the change in ear thickness in all test groups. Body weight measurements were recorded on study day 1, twice weekly and at study termination (Day 10).

At study termination, animals were sacrificed by Carbon dioxide asphyxiation. Following sacrifice, both ears from all animals were removed by cutting horizontally across the indentation at the base of the ear and were weighed.

Figure 2A:
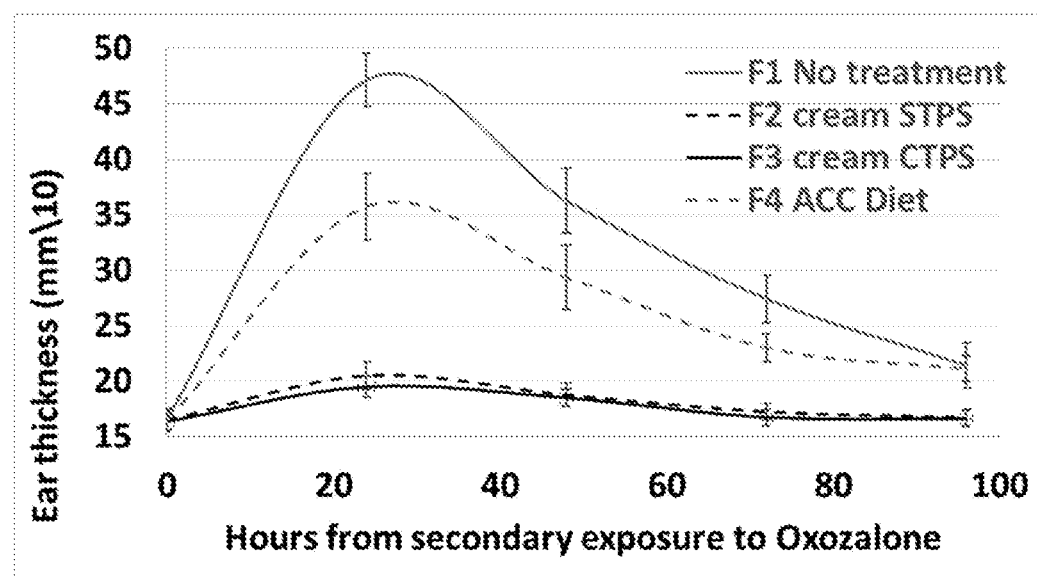
FIG. 2A. Ear thickness in a murine model of inflammation.

Results: FIG. 2A depicts ear thickness as a function of treatment from the secondary exposure to Oxazolone. As can be seen, when the ear was re-exposed to Oxazolone, a severe ear swelling was observed in group F1 which indicates inflammation development during about 24 hours following Oxazolone re-exposure. Mice that were orally administrated with ACC, developed less severe inflammation than the control group. Mice that were administrated topically with ACC based creams (F2 and F3 groups) demonstrated practically no swelling of the ear that indicates little to no inflammation development.

Figure 2B:
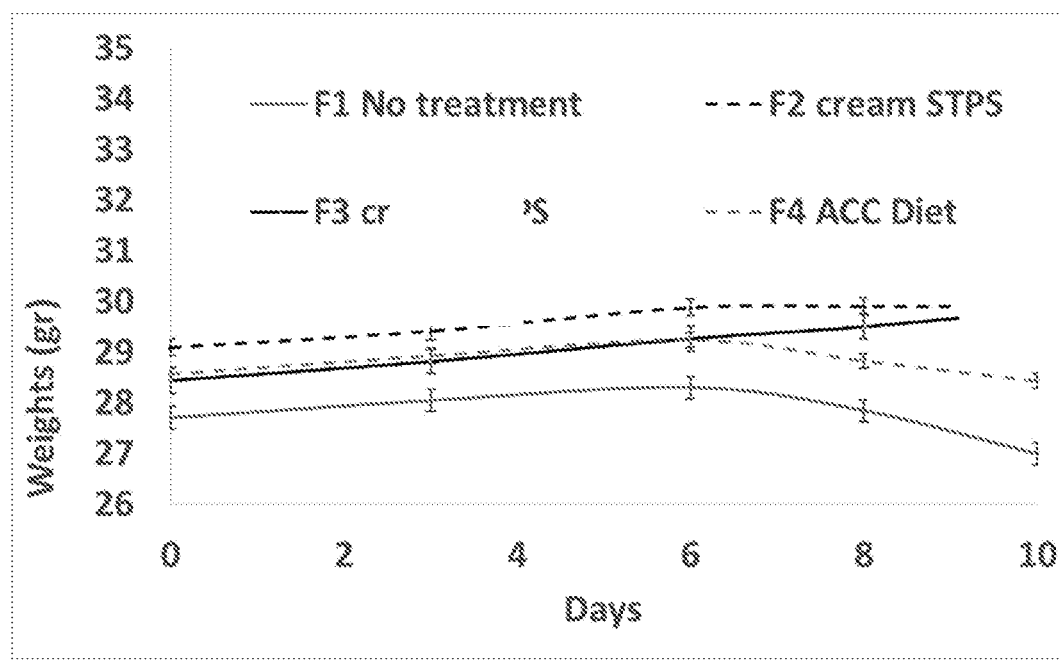
FIG. 2B. Body weight in a murine model of inflammation.

FIG. 2B shows the averaged body weights of treated mice as a function tested groups from study start initiation to study termination. No abnormality in the body weights was detected among treatment groups. A reduction in weight was observed in the untreated control group and less of a reduction was displayed in Group F4 (ACC fed group).

TABLE 4

Averaged ear weights at study end point (day 10) as a function of treatment groups.

|  | Right ear (gr) | Left ear (gr) |
| --- | --- | --- |
| 1F No treatment | 57.57 ± 6.75 | 48.57 ± 3.26 |
| 2F cream STPS | 54.13 ± 4.67 | 47.50 ± 3.93 |
| 3F cream CTPS | 54.63 ± 4.41 | 46.63 ± 3.46 |
| 4F ACC Diet | 56.00 ± 4.21 | 48.00 ± 3.63 |

All test groups demonstrated a similar ratio between right and left ear, which varied between 1.14 to 1.19.

Conclusion: This study examined the use of ACC in the treatment of a disease comprising dermal inflammation by using delayed-type hypersensitivity (DTH) model in mice. The results of this study corroborated that administration of topical ACC-based creams significantly prevented and/or reduced the swelling of the mice ear and therefore prevented or reduced inflammation development. Based on these results, it can be concluded that ACC can be used to treat and/or ameliorate inflammation, including autoimmune-related inflammation.

Example 5. Use of ACC in the Treatment and Amelioration of Skin Afflictions Formulation 9

Study design: Patients inflicted with various skin diseases and conditions, such as psoriasis, will be treated with topical ACC formulations according to the present invention several times a day (e.g. twice a day) for several weeks (e.g. four weeks) at a portion of their treatable areas. The other portion will be placebo-treated, and used as a negative control. Throughout the experiment, clinical parameters such as erythema (redness), induration (thickness) and desquamation (scaling) will be followed. Severity parameters will be measured and scaled on a scale of 0 to 4, from none to maximum. The sum of all severity parameters will then be calculated for the treatment area and the control area.

The following is an exemplary topical cream according to the principles of the present invention which may be used, in the above experiment: ACC—2.7%, Besswax—3%, Isostearyl isostearate—7%, Cyclopentasiloxane & PEG/PPG-18/18 Dimethicone—26.3%, Cyclotetrasiloxane & cyclopentasiloxane—29%, Cyclopentasiloxane & Dimethicone crosspolymer-14.5%, Hydrogenated castor oil—1%, Propylene glycol—10%, $C_{30\text{-}45}$ Alkyldimethylsilyl polypropylsilsesquioxane—2%, Dimethicone—4.5%.

The International Nomenclature of Cosmetic Ingredients (INCI) name "Cyclopentasiloxane (and) PEG/PPG-18/18 Dimethicone" refers to a mixture of 70—90% cyclopentasiloxane (decamethylcyclopentasiloxane) and 10—30% PEG/PPG-18/18 dimethicone (dimethyl, methylhydroxypropyl, ethoxylated propoxylated siloxane).

The INCI name "Cyclopentasiloxane (and) Dimethicone Crosspolymer" refers to a mixture of 70—90% cyclopentasiloxane (decamethylcyclopentasiloxane) and 10—30% dimethicone crosspolymer (dimethyl methyl hydrogen siloxane reaction products with 1,5-Hexadiene).

The name "Dimethicone", "polydimethylsiloxane" and "PDMS" are used interchangeably, and generally refer to a group of polymeric organosilicon compounds that are commonly referred to as silicones. PDMS is of the chemical formula $CH_3[Si(CH_3)_2O]_nSi(CH_3)_3$, where n is the number of repeating monomer $[(CH_3)_2SiO]$ units, a density of 965 kg/m$^3$ and assigned the CAS Registry Number 63148-62-9.

Example 6. Semi-Solid Formulations Formulations 10, 11

Toothpaste: Glycerin-70.3%, Precipitated silica—21%, Sodium lauryl sulfate—1%, Flavor-0.2%, Titanium dioxide—1%, ACC—5%, sodium carboxymethyl cellulose—1.5%.

Suppository: Solid fat (hydrogenated coco glyceride)—30%, Cocoa butter—2%, ACC—5%, Glycerin—10%, PEG400—23%, Solid fat & glycerol monooleate—15%, Solid fat & glyceryl ricinoleate & ethoxylated fatty alcohol—15%.

Example 7. Viscosity and Density Measurements Formulation 9

The viscosity of Formulation 9 (topical cream of Example 5) was measured at room temperature (24.8° C.) using Brookfield Digital Viscometer Model DV-II+Pro and Spindle #16 at different rotation speeds. The viscosity at 2 rpm is 56,208 cP, the viscosity at 1.5 rpm is 63,640 cP, and the viscosity at 1 rpm is 74,784 cP. The density of the cream is 0.97 gr/mL.

While the present invention has been particularly described, persons skilled in the art will appreciate that many variations and modifications can be made. Therefore, the invention is not to be construed as restricted to the particularly described embodiments, rather the scope, spirit and concept of the invention will be more readily understood by reference to the claims which follow.

The invention claimed is:

1. A method of treating or ameliorating a topical inflammation or a skin affliction selected from the group consisting of psoriasis, erythema (redness), induration (thickness), and desquamation (scaling) in a patient in need, the method comprising:

topically administering to the patient a therapeutically effective amount of a liquid or semi-solid non-aqueous composition comprising:

a plurality of stabilized synthetic amorphous calcium carbonate (ACC) particles as an active agent; and a non-aqueous liquid carrier in which the ACC particles are insoluble and are uniformly dispersed or suspended.

2. The method of claim 1, wherein the ACC comprises at least one agent stabilizing the ACC in amorphous form; and wherein the composition has a viscosity of above 40 centipoise (cP) at 25° C.

3. The method of claim 2, wherein the topical inflammation is associated with an auto-immune reaction or wherein the skin affliction is psoriasis.

4. The method of claim 1, wherein the active agent consists essentially of the plurality of stabilized ACC particles.

5. The method of claim 1, wherein the active agent consists of the plurality of stabilized ACC particles.

* * * * *